United States Patent [19]
Branson

[11] Patent Number: 5,877,819
[45] Date of Patent: Mar. 2, 1999

[54] MANAGING INFORMATION IN AN ENDOSCOPY SYSTEM

[76] Inventor: Philip J. Branson, Rte. Six, Box 578, Ingleside Rd., Princeton, W. Va. 24740

[21] Appl. No.: 63,671

[22] Filed: Apr. 21, 1998

Related U.S. Application Data

[60] Division of Ser. No. 478,865, Jun. 7, 1995, Pat. No. 5,740,801, which is a continuation-in-part of Ser. No. 40,633, Mar. 31, 1993, abandoned.

[51] Int. Cl.$^6$ .................................................. H04N 5/14
[52] U.S. Cl. ........................................ 348/701; 348/620
[58] Field of Search .................................. 348/701, 607, 348/619, 620; H04N 5/14

[56] References Cited

U.S. PATENT DOCUMENTS

| | | | |
|---|---|---|---|
| 4,679,084 | 7/1987 | Topper | 348/620 |
| 5,019,908 | 5/1991 | Su | 348/620 |
| 5,185,664 | 2/1993 | Darby | 348/620 |
| 5,329,317 | 7/1994 | Naimpally | 348/607 |
| 5,606,631 | 2/1997 | Weiss | 348/701 |

*Primary Examiner*—Howard Britton
*Attorney, Agent, or Firm*—Adams Law Firm, P.A.

[57] ABSTRACT

A system for acquiring images during a medical procedure and using the acquired images includes a storage device for storing, for each one of a plurality of users of the system, or for each one of a plurality of medical procedures, or for each one of a plurality of input or output devices, information that indicates one or more processing operations to be performed on images obtained by an input device. A system processor responds to an identity the user who is currently using the system by performing processing operations on the obtained images and applying the images to an output device based on the stored information that corresponds to the current user.

3 Claims, 21 Drawing Sheets

5,877,819

MANAGING INFORMATION IN AN ENDOSCOPY SYSTEM

This application is a 37 C.F.R. §1.53(b) division of U.S. patent application Ser. No. 08/478,865 filed Jun. 7, 1995, now U.S. Pat. No. 5,740,801 which is a continuation-in-part of U.S. patent application Ser. No. 08/040,633 filed Mar. 31, 1993, now abandoned.

BACKGROUND OF THE INVENTION

This invention relates to managing information in an endoscopy system, and in particular to controlling the acquisition, processing, storage, and display of endoscopic images.

During an endoscopic surgical procedure, the surgeon typically uses a video camera (or other suitable device, such as a video arthroscope) to capture images of the surgical site. The images are generally applied to a display device (such as a television monitor) for observation. In some cases, the images are stored on video tape (by, e.g., a VCR) or are converted to digital files for storage in memory or on a disk drive. Different physicians often use the video equipment in different ways.

SUMMARY OF THE INVENTION

One general aspect of this invention features a system for acquiring images during a medical procedure and using the acquired images includes a storage device for storing, for each one of a plurality of users of the system, information that indicates one or more processing operations to be performed on images obtained by an input device, and a processor that responds to an identity the user who is currently using the system by performing processing operations on the obtained images and applying the images to an output device based on the stored information that corresponds to the current user.

The stored information also indicates, for each user, a configuration of the input device and a configuration of the output device. During operation, the input and output device configurations are established in response to the identity of the current user. The configuration of the input device includes the format in which the device produces the image, and the configuration of the output device includes the format in which the device uses the image. As a result, the system can translate images obtained in one format (e.g., NTSC, RGB, Y-C, PAL, etc.) to another format for display by the output device, all according to the user-specified information in the storage device.

The system may include a plurality of input devices and multiple output devices. The storage device stores the information for each input device and each output device. During operation, the processor selectively processes images from the input devices based on the identity of the current user and the stored information. Likewise, the processor selectively applies the processed images to the output devices based on the identity of the current user and the stored information.

According to aspect of the invention, the preference database stores, for each one of a plurality of medical procedures, information that indicates one or more processing operations to be performed on images obtained by an input device, and the processor responds to the identity of the medical procedure that is currently to be performed by performing processing operations based on stored information that corresponds to the current medical procedure.

According to another aspect invention, the preference database stores, for each one of a plurality of users or each one of a plurality of medical procedures, information that indicates a script of designated images, and the processor responds to the identity of the current user or the identity of a medical procedure that is currently to be performed by causing a "script" of images to be captured based on the preference information in the database.

The information indicates, for each user or medical procedure, a sequence of images that are to be obtained during the procedure. In one embodiment, during operation, the current user is prompted to obtain the images in the sequence. This allows the user to follow pre-established scripts (stored as directed by the user) to perform tours of the surgical site according to the user's preference or according to the requirements of the current surgical procedure.

According to another aspect of the invention, the preference database stores the preference information as a plurality of linked records. A first one of the records identifies a type of the information, and a second one of the records contains data associated with that type of information.

According to another aspect of the invention, the preference database stores, for each one of a plurality of users or medical procedures, respective preference information that indicates one or more visual representations that are preferred to be applied to the output device or devices together with the images obtained by the input device or devices. The processor combines the one or more visual representations with the images obtained by the input device based on the preference information in the preference database and applies the images to the output device or devices together with the one or more visual representations.

The one or more visual representations may include text that is anti-aliased for improved appearance, graphical objects, or an additional image or images that may be obtained from an additional input device. The visual representation may possess the attribute of translucency. In certain embodiments the visual representations are prompts for prompting a user to capture images in a desired sequence. The processor may maintain an aspect ratio of the visual representations with respect to the images as the images are scaled in size, and may maintain the relative appearance of the one or more visual representations with respect to the images as the format of the images is changed. The processor may store the one or more visual representations in overlays in order not to affect the images.

In certain embodiments the visual representations are additional images the processor caused to be stored in a memory upon receipt of a save command during a medical procedure, and the processor may cause the output device or devices to display the images as a composite of postage stamp size images or as a sequence of full size images. The processor may be configured to invoke image processing on, or to delete, images selected by the user from among the images applied to the output device or devices.

According to another aspect of the invention, the preference database stores, for each one of a plurality of input devices or output devices, information that indicates one or more processing operations to be performed on the images obtained by the particular input device or to be applied to the particular output device. The processor responds to an indication of the identity of the particular input or output device by selectively performing processing operations on the images based on the information in the preference database.

According to another aspect of the invention, the preference database pre-stores, for each one of a plurality of users or medical procedures, respective preference information that indicates a preferred page layout of images. The processor receives an indication of an identity of a user or medical procedure and causes a plurality of images obtained by the input device to be arranged in the page layout based on the preference information. The preference information may indicate a preferred script of designated images that the processor causes to be captured based on the preference information, the script of images comprising the images to be arranged in the page layout.

According to another aspect of the invention, the processor performs a zooming function for increasing size of the images on the output device or device, and the processor performs the zooming function concentrically about a central point of the images. By performing the zooming function concentrically about a central point, rather than, for example, an upper left hand corner as in certain text processing systems, the processor accommodates the human tendency to focus on the center of an image.

According to another aspect of the invention, the preference database pre-stores, for each of a plurality of users, respective preference information that indicates a point about which the user prefers to have a zooming function performed The processor performs the zooming function concentrically about the point indicated by the preference information.

According to another aspect of the invention, the processor enhances visual quality of the images by histogram adjustment of the images, and adjusts the enhancement of visual quality based on the preference information corresponding to a particular user or medical procedure.

According to another aspect of the invention, a still frame buffer is provided that temporarily stores an image obtained by the input device, and a memory is provided that stores images obtained by the input device on a long-term basis. When the processor receives a freeze command it freezes in the still frame buffer an image obtained by the input device, and when the processor receives a save command it saves a frozen image in the memory.

In certain embodiments, when the processor receives a live command it causes the output device to display live images obtained by the input device. The processor can toggle between frozen and live images until a desired image is frozen and then saved in the memory.

According to another aspect of the invention, the preference database pre-stores, for each of a plurality of users or medical procedures, respective preference information that indicates a preferred conversion between a format in which the input device obtains the images and a format in which the output device communicates the image data to the medical practitioner. The processor translates the images between the two formats based on the preference information.

According to another aspect of the invention, the processor performs dynamic mathematical analysis of image data received from the input device. Based on the dynamic mathematical analysis of the image data, the processor automatically converts a format in which the input device obtains the images into a format in which the output device communicates the image data to the medical practitioner.

According to another aspect of the invention, the processor reduces interlaced noise on an interlaced video display device by reducing motion artifacts due to motion that occurs between acquisition of fields of video that comprise a video frame. At least one pixel in at least one line of a first field of video (preferably two pixels in two respective lines of the first field) is compared with at least one pixel in at least one line of a second field of video that is interlaced with the first field on the video display device. The line or lines of the first field are in close proximity to (preferably adjacent to) the line of the second field. The pixel or pixels in the first field are in close proximity to (preferably adjacent to) the pixel in the second field. The processor determining whether a difference between the value of the pixel or pixels in the first field (preferably the average of two pixels in the first field) and a value of the pixel in the second field exceeds a fixed value. If the difference between the values of the pixels exceeds the fixed value, the processor replaces the value of the pixel in the second field with a value closer to the value of the pixel or pixels in the first field (it is preferably replaced with the average of the above-mentioned two pixels in the first field). If the difference between the values of the pixels is less than the fixed value, the processor maintains the value of the pixel in the second field. These steps are performed for additional pixels in the above-mentioned line or lines of the first field and the above-mentioned line of the second field, and for additional lines of the first and second fields.

As described in more detail in the detailed description, the invention provides numerous other features and offers several advantages. Among them are:

1. a standardized platform for endoscopic video systems that allows more rapid evaluation and improvement of hardware and functionality.
2. simple acquisition and storage of still and live images from the operating room or endoscopy suite.
3. digital enhancement of acquired images for presentation in printed and film formats.
4. annotation of acquired images with text and graphics.
5. formatting and providing composites of multiple images, images and stock images, or drawings in a manner that provides spatial, logical or other context that improves the communicating value of the acquired images.
6. a stand-alone database application that allows individual doctors to maintain and retrieve images and text data.
7. an interface that allows existing office or hospital databases to manage image and text information relating to endoscopic applications.
8. allowing existing endoscopic database and endoscopy suite management systems (such as Siscope and others) to integrate imaging into their applications.
9. improving the reliability and dependability of endoscopic image and text data by facilitating simple and reliable systems for integration of the data with physician and facility work flows and hardware constraints.

In addition, the invention implements a modular architecture that allows improvement by upgrade instead of replacement. Regulatory requirements can often be satisfied by a modification to an existing filing, as opposed to a de novo filing.

Other features and advantages of the invention will become apparent from the following detailed description, and from the claims.

DETAILED DESCRIPTION

Figure 1:
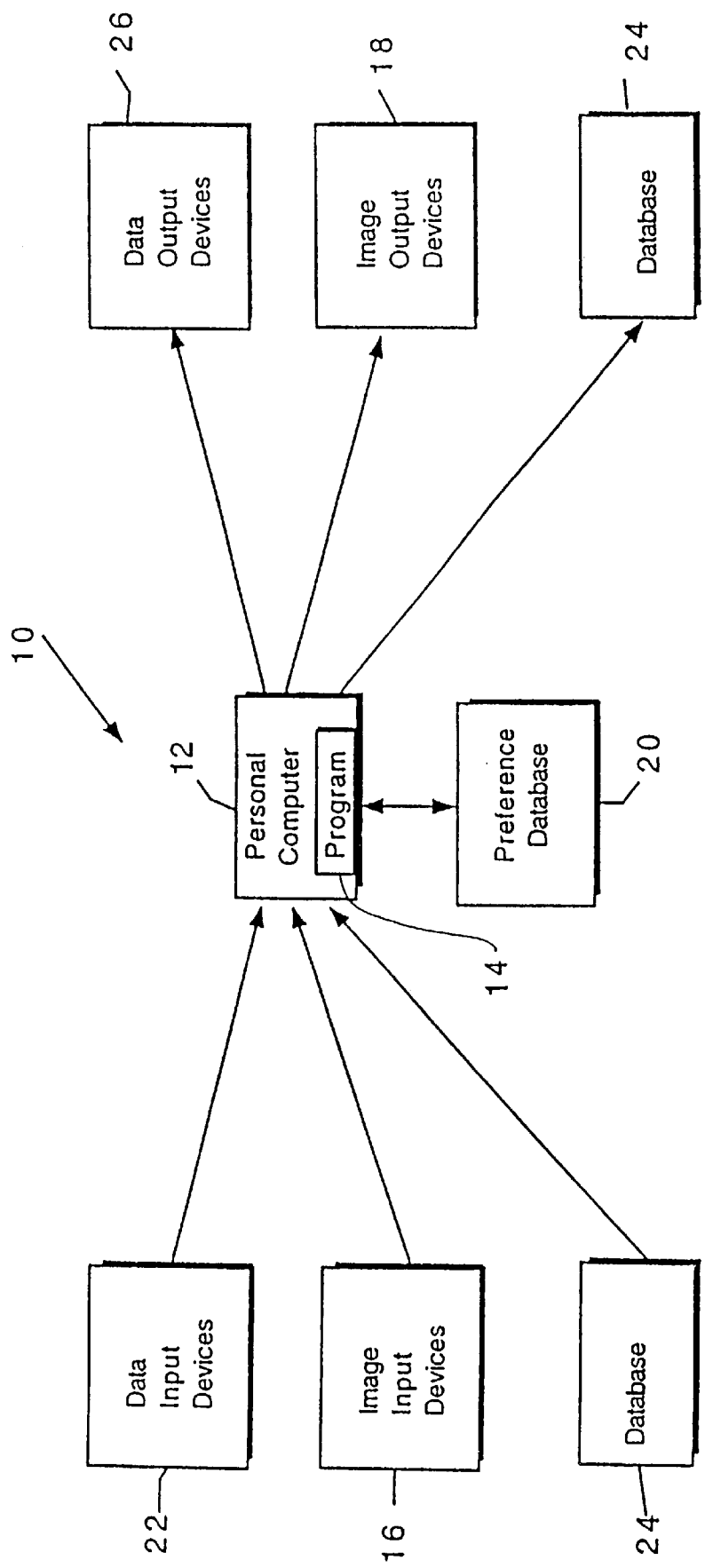
FIG. 1 is a block diagram of a system for managing endoscopy information according to the present invention.

Referring to FIG. 1, endoscopic procedure management system 10 employs a personal computer 12 that executes a stored program 14 to configure and manage all devices used by a physician during endoscopy. In particular, personal computer 12 receives images generated by one or more image input devices 16, processes the images according to the preferences of the physician performing the endoscopic procedure, and transmits the processed images to one or more image output devices 18 for display or storage.

Personal computer 12 obtains information concerning the physician's preferences about the processing, display, and storage of the images from a preference database 20. As described in more detail below, preference database 20 is organized by physician—that is, the preferences of each physician recognized by system 10 as to the image processing and the configuration and operation of image input devices 16 and image output devices 18 are stored in preference database 20 according to the identity of the physician and according to the various procedures performed by the physician. As a result, when a physician logs onto system 10 (as described below) and identifies the endoscopic procedure that he or she is to perform, host computer 12 configures image input devices 16 and image output devices 18 and controls the processing of the obtained images according to the information stored in preference database 20. Examples of information contained in the preference database include identification of available input and output devices, the scan rate and resolution of video input and video display devices, video gain, offset, and color parameters, light level reference for comparison and adjustment of light level, the format with which images obtained during a tour (described below) are to be displayed, and the format with which images are to be displayed on a video printing device.

A wide variety of image input devices 16 can be used with endoscopic procedure management system 10. For example, image input devices 16 include video endoscopes, cameras (including endoscopic video cameras and other types of video cameras), video cassette recorders (VCRs), X-ray scanners (which convert X-ray films to digital files), digital X-ray acquisition apparatus (which convert X-ray photons to a digital bitstream or file), fluoroscopes, CT scanners, MRI scanners, ultrasound scanners, RS170 video signal devices, ccd devices, and other types of scanners (handheld or otherwise).

Likewise, several different types of image output devices 18 can be connected to system 10. Examples include cathode ray tube (CRT) displays, television monitors, LCD panels and screens, EMM memory, and disk memory, digital film recorders, postscript color printers, raster-driven film recorders, and faster-driven printers. The displays may use the RS170 format (i.e., RGB, Y-C, NTSC, PAL, or the PAL equivalent of Y-C), or alternatively may be non-RS170 devices (interlaced and non-interlaced display devices).

As described in detail below, visualization input and display subsystems connected with the personal computer 12, whether internal, or external, are supported by defined communication protocols (e.g., horizontal and vertical synch, interlaced vs. non-interlaced display, scan speed and spatial and color resolution) that are stored in the database.

In addition, personal computer 12 also receives data and commands from one or more data input devices 22.

Data input devices 22 can include computing devices such as laptop and palmtop computers, pen-based command systems, or computer networks. The data and commands from such computing devices function primarily to allow data entered outside the operating room to be used within the operating room. For example, a surgeon's assistant may enter identification information about a day's work on such a computing device to load that information into endoscopic procedure management system 10. In this way, operating room data entry can be minimized.

Data input devices 22 can also include programmable input devices (such as infrared remote control units), voice recognition systems, and pointing devices such as a keyboard, mouse, trackball, airmouse, light pen, touch screen, and tablet. These programmable input devices operate by a software-mediated control step. In particular, the programmable input devices generate generic commands, and the response of endoscopic procedure management system 10 is stored in software. Use of these programmable input devices can initiate a simple or complex sequence of events.

All of these data input devices 22 allow the physician (or another user located, e.g., in the sterile field) to manage the operation of system 10, as described in detail below.

Personal computer 12 can also be connected (either directly or via a network or modem) to one or more unrelated databases 24 to receive patient and other information. Examples of databases 24 include hospital information systems and local databases located in the physicians'offices, patient information databases, external office databases, external hospital databases, external database conversion utilities, and external high-capacity storage devices.

Numerous data output devices 26 are also connected to personal computer 12 for receiving data concerning the operation of system 10 (e.g., reports). Personal computer 12 also sends data to one or more of databases 24 for storage. Examples of data output devices 26 include laptop, palmtop, and pen-based computer systems, printers, disk drives, PCMCIA memory cards, modems, and network communications devices.

Figure 2:
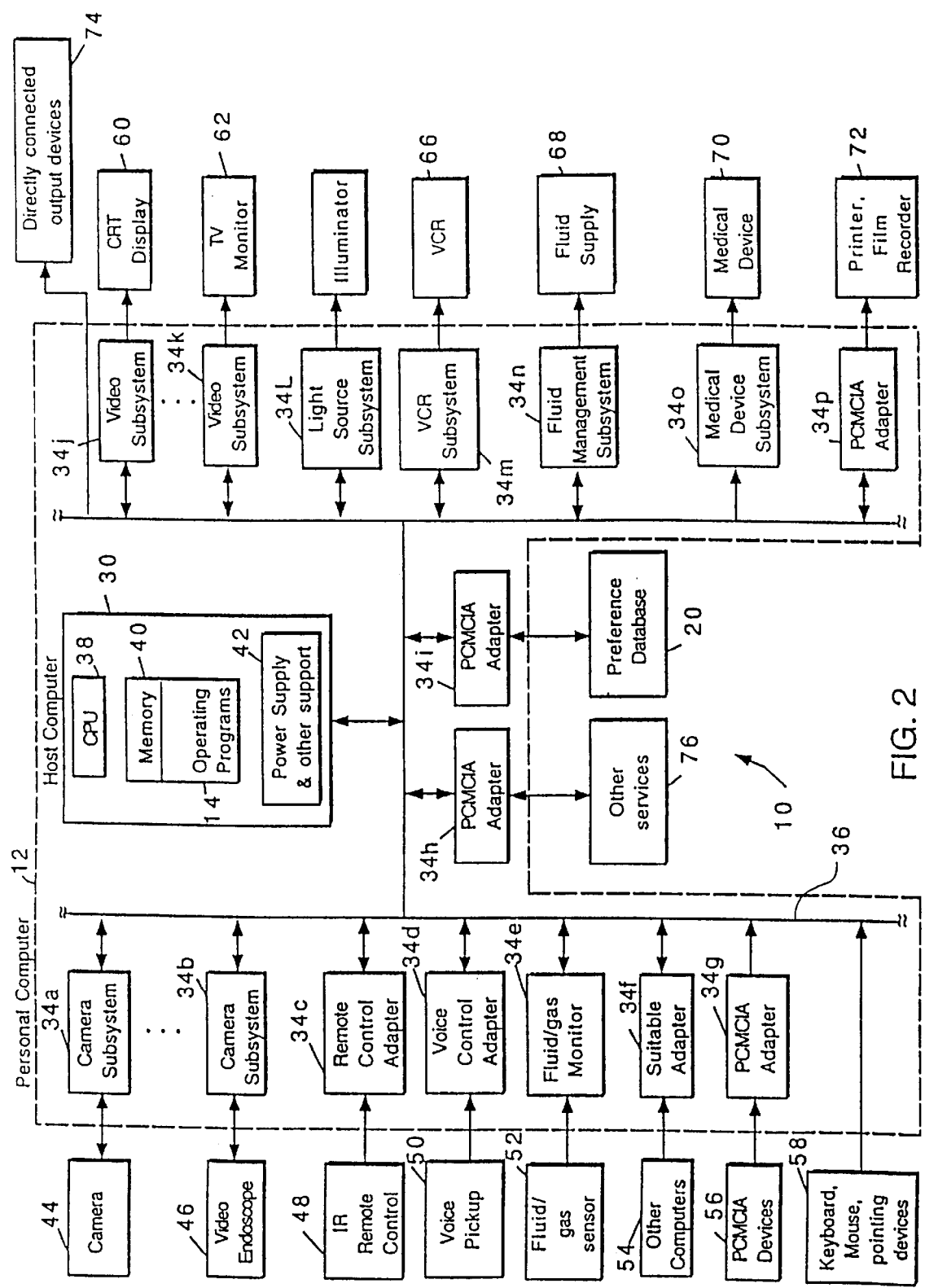
FIG. 2 shows one possible configuration of the system of FIG. 1.

Referring also to FIG. 2, one possible configuration of system 10 is shown. Personal computer 12 includes a host processor 30 and a series of subsystems or adapters 34a–34p (hereinafter generally referred to as 34) each of which is connected to host processor 30 by a bus 36 (if the configuration of personal computer 12 so dictates, bus 36 is replaced by a backplane). If needed, one or more subsystems 34 can also be connected to host processor 30 or to each other via a local bus (not shown).

Host processor 30 provides an industry standard platform that supplies a common power supply, a computing function (CPU 38), memory and storage devices 40, mechanical support and cooling functions 42. Subsystems 34 gain access to any or all of these services via bus 36 in a motherboard implementation (or the backplane in a backplane implementation). Other systems outside the physical housing of personal computer 12 can gain access via subsystems 34 that externalize these functions from personal computer 12.

Host processor 30 is a 486-66, Pentium, or 686 based machine; alternatively, host processor 30 may be implemented as a workstation. Standard ISA bus architecture is used, but EISA or PCI architecture or others can be selected instead. In the motherboard configuration, the memory and CPU and expansion slots are on a single board. In the backplane configuration, power and communication occur via the backplane, and CPU 38 and memory 40 plug into the backplane like an adapter.

Host processor 30 contains a special version of a BIOS (Basic Input/Output System), located on a ROM chip, that specifies the setup parameters of a generic personal computer in such a way that operation of a system storage disk and connected devices can be restored despite failures that would render a standard personal computer useless. The CMOS settings on a generic personal computer are generic, and the setup parameters are held in CMOS, which depends on battery backup and system integrity to persist. If a peripheral shorts, or the backup battery goes down, at least some of the system settings might have to be re-entered before the system can be used. By restoring the CMOS with the ROM, even custom setups of the PC can be re-entered by software so that the PC can be fully recovered from the majority of problems that could bring a PC down.

Subsystems 34 and host processor 30 communicate in a bi-directional fashion over bus 36. Each issues and receives commands, status and other information. Host processor software control 14 integrates and regulates the flow of information, and hence the operation of subsystems 34 and the input/output devices. Communications that conform to platform standards can be handled by bus 36. Specialized or nonstandard communication can be handled by local buses, such as a local video bus (not shown). A local bus provides specialized communication of limited scope. Overall function of the local bus can be governed by communication that occurs over bus 36.

The communication afforded by bus 36 allows for software control of the specific functions of system 10. Software control of specific functions can be based on data entered into the preference database, operator instructions received via data input devices, or on feedback from the subsystems. For example, preference database 20 contains information regarding video gain and offset, image format preferences, and text data required for display of images obtained during endoscopy. Settings or user preferences can be accommodated and tailored to the (typically different) specifications of each physician. By specifying a particular procedure or a particular surgeon it is possible to cause preferences associated with the identity of the surgeon or the procedure to be loaded. In addition, the operator can modify the preference settings by direct instructions communicated via a system input device. Furthermore, the system itself can modify the preference settings. In system-mediated modification, the system responds to specified parameters based on the state of the system or a portion of the system. For example, the system allows for a histogram, or other mathematical process to be performed on an image. Based on the result of the mathematical process, the system software can send commands or data to the camera or video signal source. The commands result in optimization of the acquired video. Other system-generated input, such as video level, color composition, or most recent operator interactions, can be used to specify a system response. Thus, preferences can be modified by the operator, or dynamically by system 10. Thus, the system responds to database entries (procedure or user ID), calculated entries (histogram of an image, video level via defined relationships stored in the preference database), and user input (keyboard, mouse, or other pointing device).

As discussed below, multiple control devices are supported. An infra-red, programmable handheld remote control 48 provides operator interaction from a sterile field. Hard-wired switches connected by wires to the operative field can also be used. The system also provides for multiple inputs from touchscreens, mouse, light pens and other relative and absolute pointing devices 58.

The system is structured to be platform independent. The software provided for the system is organized so that portions of the code that are hardware dependent can be easily replaced. As CPU and adapter subsystems are improved or changed, a means is provided to allow simple integration of the new devices. Identifications of input and output devices, as well as specifications, are stored in preference database 20, and this stored information controls device-specific outputs. For example, 24 bit color images can be processed to display on a 64 color gray scale device based on the database preferences stored in database 20.

The platform independence is related to separation of hardware-dependent code from hardware-independent code. In one embodiment the system runs under DOS, but with simple modification could run under Windows, OS/2, UNIX or other operating systems or hardware platforms. This is accomplished by separating generic file system calls, calculating functions, display operations (blitting) from operating system or hardware dependent functions. In this way, a change of the database utility, driver utility or any other segment of the program can be done without altering the main body of the code.

As is discussed below, the software system includes heuristic systems that allow multiple complex functions to be controlled automatically or with minimal and simple operator input.

The host 30/subsystem 34 architecture allows for both standardized communication therebetween via bus 36 and the sharing of resources (such as memory and processing functions). Subsystems 34 identify themselves to host processor 30, send queries to and respond to queries from host processor 30, and provide signal and control outputs to host processor 30.

Communication occurs over bus 36 between host processor 30 and subsystems 34 and between the subsystems 34 themselves. As can be appreciated from FIG. 2, inputs can be applied to personal computer 12 either through the subsystems (e.g., subsystems 34a–34g) or directly to host processor 30. Likewise, output signals and data are produced by both host processor 30 and the subsystems (e.g., subsystems 34j–34p).

FIG. 2 illustrates several different types of subsystems 34. Camera subsystems 34a, 34b provide host interfaces for a camera 44 and a video endoscope 46. Remote control adapter 34c interfaces a remote control unit 48 (infrared or otherwise) to host processor 30. The physician can control system 10 using voice commands that are relayed from voice pickup 50 to host processor 30 by voice control adapter 34d. A fluid/gas monitor 34e relays signals from a fluid gas sensor 52 in the sterile field to host 30. Laptop, palmtop, and other computing devices 54, and pointing devices communicate with host processor 30 via suitable adapters 34f. PCMCIA devices 56 (discussed below) are interfaced with host processor by PCMCIA adapters 34g. Other input devices 58 (such as a keyboard and pointing devices such as a mouse) are connected via specific interfaces directly to bus 36.

Video subsystems 34j, 34k provide interfaces with a CRT display 60 and a television monitor 62. The level of light provided in the surgical field by an illuminator 64 is controlled by light source subsystem 34l. A VCR subsystem 34m supplies image signals to a VCR 66. The operation of devices used in the surgical field, such as fluid supply 68 and one or more medical devices 70 (e.g., surgical tools such as shavers, abraders, end cutters, etc.), are controlled via fluid management subsystem 34n and medical device subsystem 34o, respectively. Other output devices, such as printers and film recorders 72, are driven by host processor 30 via one or more PCMCIA adapters 34p, while some output devices 74 can be connected directly to bus 36.

Preference database 20 can also be connected to host processor 30 via a PCMCIA adapter 34i. A PCMCIA adapter 34h is used to connect host processor 30 to units 76 that provide other services. Examples of other units 76 include storage devices, e.g., disk drives, memories (such as so-called "flash memories"), disk drives, and network adapters (for wire, wireless, RF, or optical networks). Any device that conforms to the PCMCIA connectivity standard (or any other suitable standard, such as JEIDA) can be connected to personal computer 12 in this fashion. In addition, any suitable port of host processor 30 (e.g., serial, parallel, SCSI, etc.) can be used to provide I/O capability.

Camera subsystems 34a and 34b utilize a PC standard adapter card configuration containing circuitry to process electrical signals generated by a device responding to changes in available light, for example a charge coupled device. The circuitry supplies power and synchronization for the image acquisition device, and provides a means to communicate with the host system. The host system is able to download alignment parameters to the CCD controller, and interpret commands and status returned from the subsystem to the CPU. Camera 44 and video endoscope 46 are self-contained units that acquire an image, and produce a standard video or digital signal that can be decoded or interpreted by the video subsystem to produce images on a display device. The system has a control mechanism, for example, RS232, with which the host can issue commands and receive status from the camera system as described above.

Remote control adapter 34c interfaces with infrared remote control 48, which includes a transmitter and a receiver. The transmitter is a handheld unit that emits infrared radiation in a predictable manner, based on instructions stored within the unit. The Receiver detects and interprets infrared emissions of the transmitter, and produces machine readable commands that are communicated to the CPU, which compares the commands to taxonomy contained in preference database 20 and executes the command based on the information contained in the preference database.

Voice Control Adapter 34d accepts and processes audio input, from a microphone, and performs interpretation, resulting in machine-readable signals that are transferred to the CPU. The function of the voice control adapter is to translate spoken words or speech into machine-readable input commands. The machine-readable commands can be used as a means to implement controls. Alternately, the voice recognition can be used to enter text data into the database.

Fluid/gas monitor 34e interfaces with fluid/gas sensor 52, which is, in one embodiment, an insufflator, i.e., a device that controls flow and pressure of a medical device into body cavities. It communicates with the CPU by RS232 or a device-specific communication protocol. The CPU translates database preference values to commands that configure the pressure and flow parameters on the device. The device issues status and error messages to the CPU via the same communicating means.

Adapter 34f is a device-specific adapter for receiving information from, or transmitting information to other computers, i.e., main-frame hospital computers, personal computer networks, handheld computers. This interface is a means for exchange of text and image data.

PCMCIA adapters 34g utilize a standard pin and socket configuration to interface to a wide variety of devices that are identified to the host system by the insertion of the device. The PCMCIA adapter can accept specific hardware to perform modem, network, storage or other functions. The CPU side of the interface is standard, and conforms to the PCMCIA standard for power and data exchange.

Directly connected output devices 74 can include video monitors and CRT displays.

Details of video subsystems 34j and 34k are set forth below in connection with FIGS. 3, 4, and 5.

Light source subsystem 34l processes signals generated by the video subsystem, and outputs an electrical potential used to adjust the intensity of light provided by the illuminator. Light intensity is controlled by closing an aperture, or decreasing lamp supply voltage.

Details of VCR subsystem 34m and VCR 66 are set forth elsewhere in this application.

Fluid management subsystem 34n interfaces with fluid supply 68, which is a pump and suction apparatus to provide control of volume and pressure of irrigation fluids introduced into body cavities. The system senses and reports pressure, flow, and status. The system interfaces with the CPU and preference database via a RS232 protocol, or device specific protocol. Database preferences for pressure, flow and operations are communicated to the device, and status is returned by the device to the CPU. Pressure and flow parameters are controlled based on user identification, procedure, or a combination of user and procedure.

Medical device subsystem 34o is a generic interface to conform to the evolving medical device control standard, whereby other pumping, light, or other medical device can be operated via a standard interface communication between the CPU and the device. The system supports standard or non-standard interfaces including serial, parallel, SCSI, GPIB or other protocols.

PCMCIA adapters 34p interface with printers and film recorders 72, which can be controlled via a parallel, SCSI, or GPIB interface, coupled with a device-specific software driver. As in all devices in the system, the device-specific driver translates generic commands from the system into specific commands understood by the device. The device driver also interprets device specific-status reports, translating them to specific or generic reports and requests that are interpreted by the CPU, and result in continued operation, or error reporting.

Printers and film recorders 72 can include a post script printer. Conforming to Adobe post script level 2 page description language, a text file containing information sufficient to allow rendering of the image is transmitted to the printer. The description contains all necessary data to allow the raster image processor to size, scale, and position text and images. Data is transmitted in a device-dependent manner as either binary information or ASCII character strings.

In connection with the use of film recorders, raster information is transformed to the appropriate resolution by a bicubic interpolation routine. Sizing and gamma correction is done using standard algorithms. The image is separated into red, green, and blue components. Using device-specific look-up tables, the color-specific intensity of each data point is translated into a film-specific exposure time. The data is downloaded to the imaging device that accomplishes exposure of the film in a red, green, and blue cycle.

Printers and film recorders 72 can include a 24-bit true-color VGA device. Raster information is presented to one of several supported display devices by translating pixel information and CPU instructions to the display chip, using protocol provided by the chip designer, manufacturer.

Figure 3:
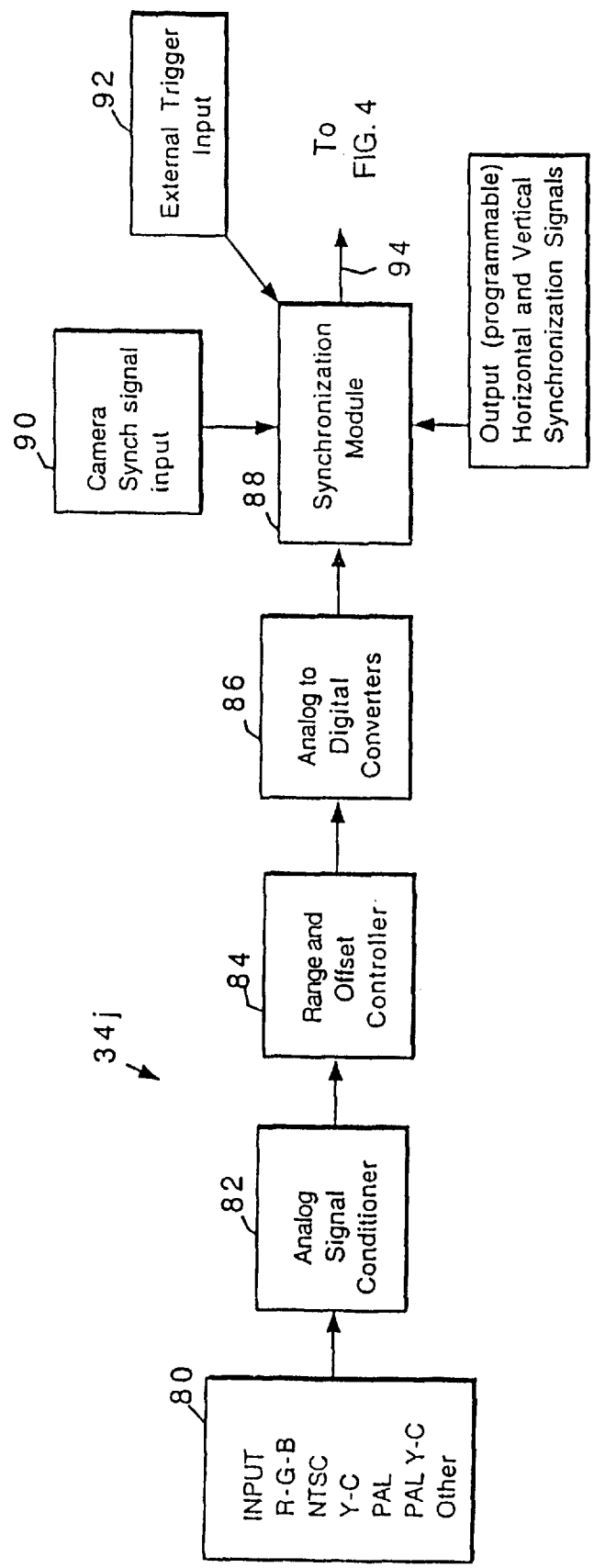
FIGS. 3 and 4 shows details of a subsystem used in FIG. 2.
Figure 4:
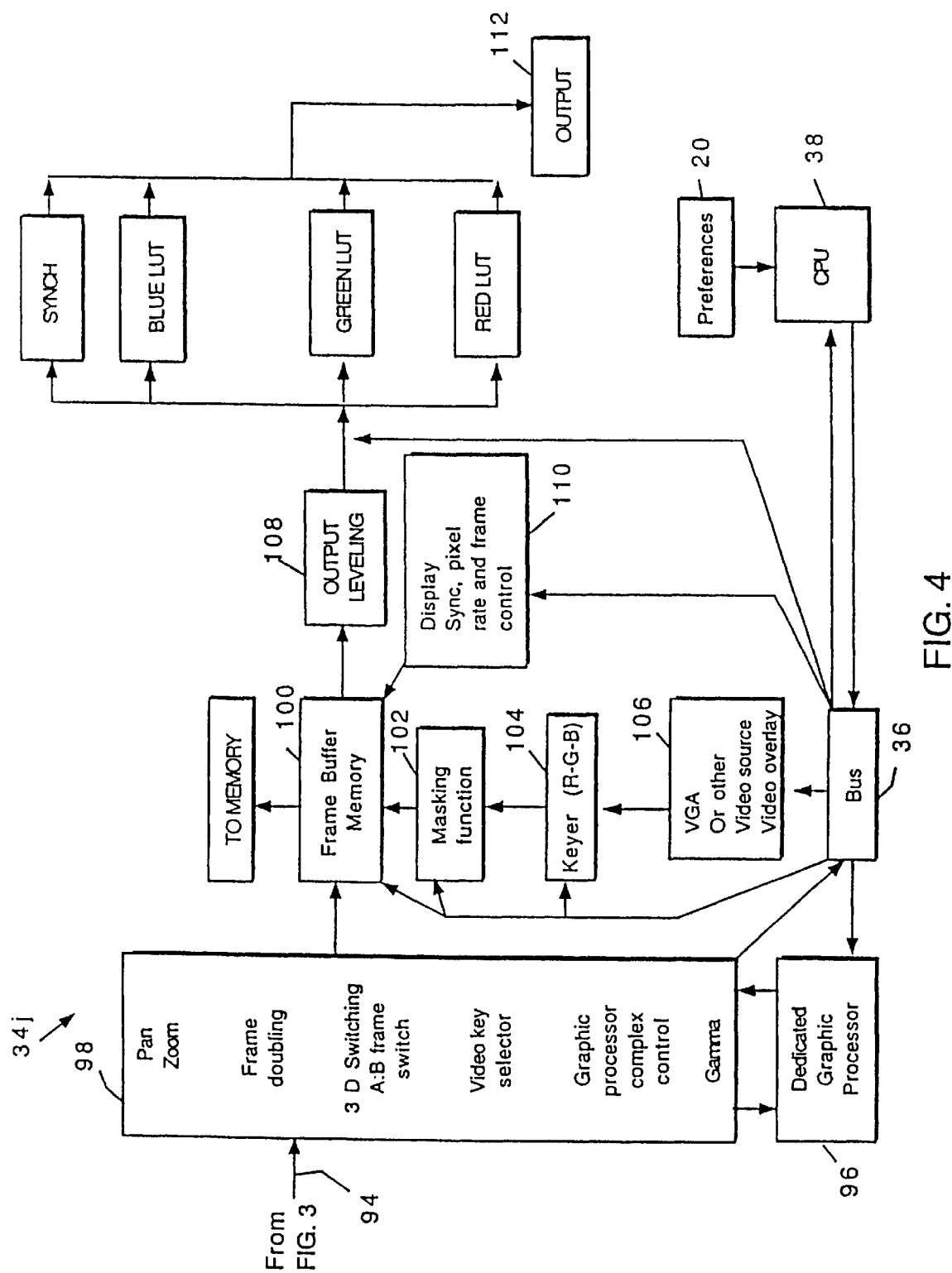
Figure 5:
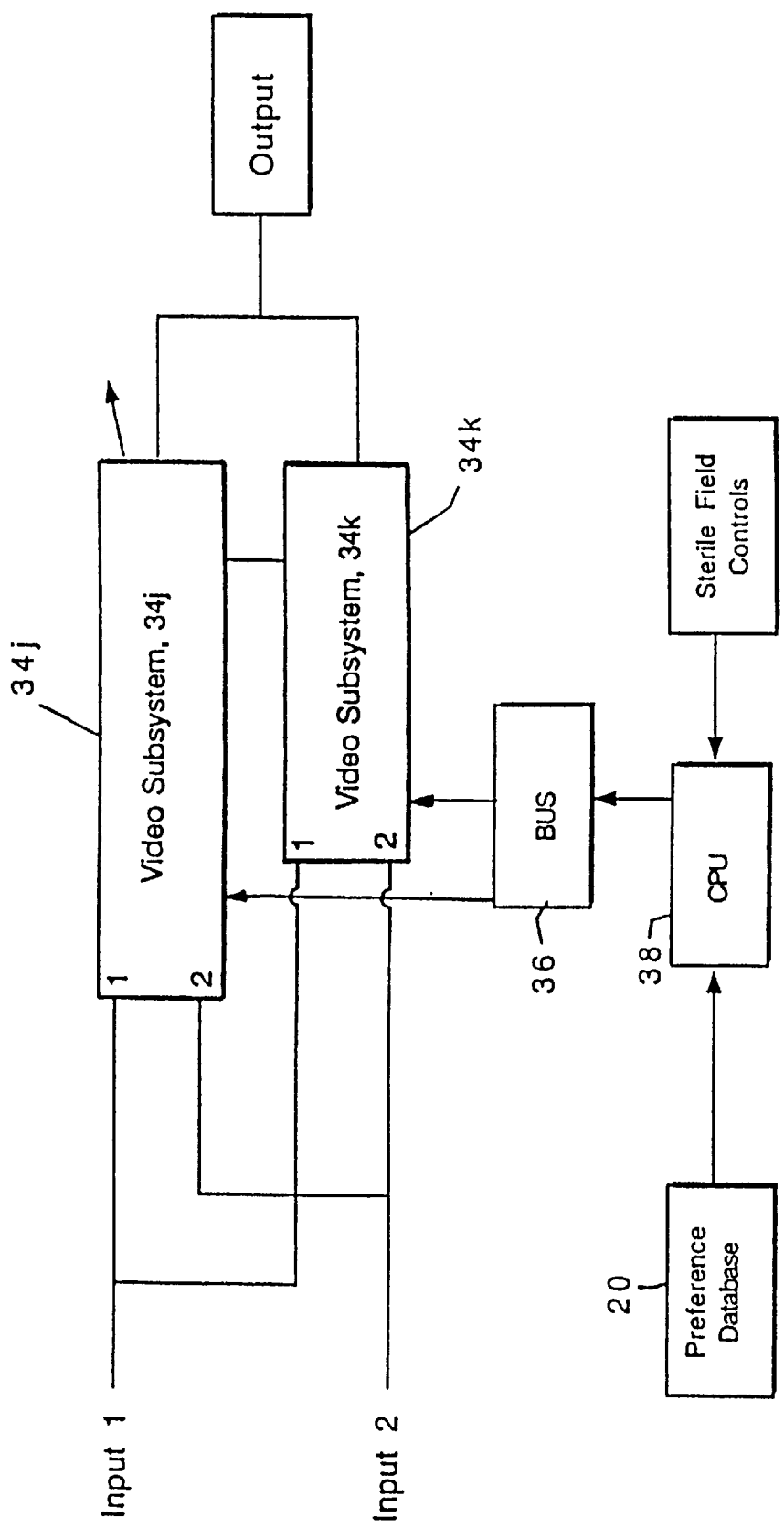
FIG. 5 shows two subsystems of FIG. 2 connected in parallel for so-called "picture-in-picture" display of images.

Referring to FIGS. 3 and 4, details of video subsystem 34j are shown (it will be understood that video subsystem 34k is identical to subsystem 34j). Video subsystem 34j resides on full length PC card, and contains the necessary processors and memory to allow real-time gain and offset control, and matching of multiple inputs to multiple output timing specifications for display, pan, zoom, video overlay and digital signal processing. The system contains a resident, read only memory BIOS that allows this subsystem to operate in a limited fashion as long as power is good, even if other components of the host system 10 fail.

The functions of video subsystem 34j are performed on the board in response to software commands to the board. The multiple functions of video subsystem 34j include:

1. Encoding and decoding RGB, NTSC, Y-C and PAL;
2. Synchronization functions: acquisition synch, display synch, pixel clock control and synch conversion;
3. Digital signal processing (DSP);
4. Image manipulation operations such as zooming and panning;
5. Drawing graphics such as boxes and lines;
6. Control of video memory (i.e., in, out);
7. Controlling aspect ratio;
8. Select between display of:
   (a) the image that currently resides in the frame buffer, or
   (b) the live image;
9. Definition of input and display device parameters;
10. Acquisition and display look up table controls;
11. Acquisition and display weighing, adjustment;
12. Color extraction and object recognition functions;
13. Masking functions;
14. Video display/overlay keying;
15. Convolution;
16. Management of programmable events;
17. Mathematical operations on video signals;
18. Inter-image operations and manipulations;
19. Histogram extractions from images;
20. Operations on defined areas of interest;
21. Morphologic manipulation of image information;
22. Extraction of a profile of pixels for a defined sample range;
23. Control of pixel flow between host and subsystem memory;
24. Extraction of the run-length of an image;
25. Controlling the transfer of host and adapter memory buffer lines;
26. Controlling the range and offset of analog-to-digital converter;
27. Write and position text;
28. Analog-to-digital conversion;
29. Digital-to-analog conversion.

The majority of the functions performed on the video subsystem 34j are controlled by the Texas Instrument 34010 chip. Other chips and functions can be added including DSP chips that can perform some of the histogram functions (described below) or other calculating functions more rapidly.

Many of these functions may be reproduced in software for still image processing and real-time processing in virtual memory of host processor 30.

As shown in FIGS. 3 and 4, video subsystem 34j receives an image 80 (to be displayed, e.g., on CRT display 60) in any suitable format (such as RGB, NTSC, Y-C, PAL, or PAL Y-C). The image is applied through an analog signal conditioner 82 and a range and offset controller 84 to an analog-to-digital converter 86. The digitized image is applied to a synchronization module 88, which also receives as inputs a camera synch signal 90 (and possibly other external triggers 92). Synchronization module 88 can also generate synch signals for one or more input devices (such as cameras). The synchronized image signal 94 produced by module 88 is passed to graphics processor 96.

Graphics processor 96 performs the graphical functions described above (several of which are listed in box 98) on image signal 94. The image produced by graphics processor 96 is sent to frame buffer memory 100 for subsequent display. Graphics processor 96 also returns information about the live, processed image to host CPU 38 via bus 36 (or via a local bus within personal computer 12). CPU 38 responds to this information, and to the display preferences (from preference database 20) of the particular physician who is using system 10, by dynamically adjusting one or more display parameters of the live image in the video subsystem. The system can also send instructions and setup parameters to the video input device.

Histogram processes are standard mathematical distributions of the digital values representing each of the red, green and blue components of each pixel. Histogram and distribution functions are resident in the graphics processor 96. In response to a command from the CPU 38, via bus 36, the graphics processor will return a table of values corresponding to the output of the histogram operation, or a selected set of values as specified. These functions are part of the standard functionality of the TMS 34010 processing chip. Some or all of these functions can be reproduced on the CPU using software emulation of the graphic processor function. Software program 14 compares the result of the specified operation returned by the graphic processor 96 to a taxonomy of values stored in the preference database 20, and executes the response corresponding to the values. The taxonomy of values can correspond to user, system, or other designations that can be modified by the user.

In response to histogram calculation on an area of the image, the system can download new camera (input source) configuration tables. This results in correction of the input signal, as compared to enhancement of the signal that occurs on the video subsystem card in the digital realm.

Examples of the processing performed by CPU 38 on the image include masking 102, keying 104, VGA-, video source-, or CPU generated-overlaying 106, and output leveling 108.

Masking involves selection of portions of an image by color or edge detection. Masked areas of the image can either be the target for further processing or excluded from further processing.

Keying involves selection of areas of the image by color attribute. The area of the image with a designated pixel or color value can be operated on (e.g., replaced with other pixels, changed to another pixel color or value, etc.). Keying operations are performed by sampling areas of the image designated by a preference stored in the database or program itself, sampling the area for digital color level in R,G,B or other suitable mode, and selecting or excluding pixels from the image matrix based on the selection criteria. For example, the black border around an arthroscopic image can be excluded from image processing operations by sampling the black border, selecting it and excluding it from further operations.

Overlaying involves displaying text, graphics, or other images on top of the image. This method is used for display of status and'some display of text.

In addition, CPU 38 adjusts (where required by the preferences from database 20) such display parameters as display synch, pixel rate, and frame control (110). The resulting image information (consisting, e.g., of BLUE LUT, GREEN LUT, RED LUT, and SYNCH) provides the output 112 of video subsystem 34j.

The zooming function performed by graphics processor 96 allows real-time images or still images to be magnified by a user-specified value. The zoom can occur concentrically about a point specified by the user or preference database. The usual specification for zoom concentricity is the central point of the image, although any point may be specified. Image processing is done to allow the highest quality view of the magnified image. This is either a specific hardware routine or can be performed in software in a virtual frame buffer. In this implementation, a zoom command issues a hardware call to the graphics processor 96. The software call specifies the magnification value, as well as the x,y coordinates of the location of the zoom, which in one implementation is the center of the image. The zoom occurs by pixel replication, resulting in apparent magnification of the displayed image.

In addition, execution of the zoom function adjusts an electrical potential output (not separately shown) that allows any external device to interpret the potential and adjust light intensity so that the light level is appropriate to the magnified field of view. The electrical potential is related to the luminance or brightness of the reduced field of view caused by the zoom, as opposed to the entire incoming video signal. This allows appropriate light level for the area being visualized.

If an image is saved (i.e., "captured," as discussed below) during zooming, a tag is placed in the image file header. The tag alerts an output device that uses the image file to display or print the image as zoomed, i.e., in the same manner in which the image was displayed to the user at the time of capture. Alternately, the device may ignore the tag, and may print the image without modification, if this is so specified in the preference database.

In the non-zoom, or 1:1 mode, area of interest processing can be used to generate a light source control potential that is weighted for a defined area that is a subset of the entire viewing area. This area of interest can be dynamically changed by an algorithm in the software. Area of interest processing is implemented by selecting a defined set of pixels that is a subset of all pixels that comprise a given frame. In one implementation, a circular or square subsample of pixels is selected by an instruction from the CPU to graphics processor 96 that specifies the range of pixels, as well as the X,Y location of the offset of the selected pixel set. This same selection technique is also used to perform comparisons of several selected areas of the image. For example, in an arthroscopic procedure, the subsample area is defined as a circle in the center of the image, with a diameter equal to the smallest dimension of the imaging area. Image processes, and all image functions of the graphic processor 96, or software emulation of these functions, can be performed on the selected area in the same manner as they are performed on an entire image.

System 10 also provides for manual, user-prompted control of gain and offset, specification of multiple values for gain and offset in preference database 20, and a real-time process for automatic context and value-sensitive means for control of gain and offset. Automatic adjustment is accomplished by mathematic processing of the signal in areas of interest on the live or incoming video. In one implementation, the individual RGB gain and offset parameters are reduced to user selected controls for brightness, contrast, and hue. The brightness, contrast, and hue functions allow the user to adjust multiple video parameters in a linear or non-linear fashion in a familiar, and simple manner. The combination functions of contrast, hue, and brightness simultaneously adjust multiple gain and offset features in the R-G-B domain, resulting in image changes that mimic the adjustment of a television. The system may also contain a number of preset gain and offset groupings. The groupings can be related to specialty or procedure. These presets may be accessed by sequential, single key offset adjustment commands from the remote control. The system provides a standard, or default setting that produces an output image that is the same as or similar to the input video signal. The gain and offset settings are implemented by modification of the input or output lookup tables (LUT's), processes implemented by the dedicated graphics processor, limits on the digital-to-analog ar analog-to-digital convertors, or chip-specific instructions to the video encoding or decoding hardware.

For example, there may be several gain/offset combinations that are useful for a gallbladder. A single keypress on the remote would cycle through the preset settings. The operating range and incremental change per press can be set by specialty, surgeon, or procedure. This is considerably more flexible and functional than adjusting the video using switches or dials, which are impractical to use during a procedure.

An important feature of this system is monitoring for video signal. The software can monitor when the board of the video subsystem has live video input. Lack of live video input generates a message to the user to correct the deficiency.

Another important feature is the direct video signal bypass. Because the system is placed in the video stream, failure of the system could interfere with completion of the procedure. For this reason, a second path is provided for video directly from the video source to the screen so that the procedure can continue even if these other functions added by the system are lost.

The architecture of video subsystem 34j allows images to be displayed in a variety of formats according to the preferences of the physicians that use system 10. For example, referring also to FIG. 5, a pair of video subsystems 34j, 34k are wire-ored together to produce a "picture-in-picture" output for display. Both images are applied to each video subsystem 34j, 34k. Each subsystem 34j, 34k processes one image and simply monitors the other image for synchronization purposes. For example, video subsystem 34j processes input 1 and monitors input 2, leaving it to video subsystem 34k to process input 2 (and monitor input 1). More than two inputs can be used, if desired.

The image inputs may be either synchronous or asynchronous. That is, video signal synchronization can occur at the inputs to subsystems 34j, 34k via a system-generated synch signal, or at the level of subsystems 34l, 34k in display management by CPU 38. Host CPU 38 and program 14 control the output video, the asynchronous video signals to a single output display. The wired-or connection provides a current drive that adds the two image signals together. The sizing, location, and priorities of the two images are selected, switched, and defined based on the preferences set forth in database 20 and the sterile field controls (e.g., remote control 48, FIG. 2) operated by the physician or other user. Each signal input can be individually processed and controlled with the multiple image and signal processing functions discussed above. The CPU commands for handling the multiple images are in addition to the commands listed above, and are relayed to the subsystems 34j, 34k via bus 36.

In particular, priorities of location of images can be controlled by software-controlled placement of a "black" or "blank" signal, outside the value of pixels found in a typical image in the output image. At the output stage, the video signals are combined or added, so that the second (or third, etc.) live video signal is added to the black or blank area of the main image. The resident image processor, which processes the signal for an image designated to occupy less than the full available display, can handle reduction of the image display size. The reduction of display size can be accomplished by a pixel or line subsampling, or pixel/line combination by a mathematical weighing of pixels. This results in more accurate spatial and color representation in the image, even though the actual number of pixels used to display the image is diminished.

Alternatively, a lower-cost implementation of picture in picture, or simultaneous display of two image input sources on the same display, can be accomplished by a software-controlled video switch applied at the input side of a single video subsystem 34j. The video switch contains standard circuitry for the combination of an analog video signal. In addition, a software-controlled switch toggles between interposition of the video switching apparatus, or direct input to subsystem signal communication from the primary video input source. When the switch is implemented, the input signal to the video subsystem will consist of the combined signal from both video sources. The composition of the combined signal will be dictated by the video switch circuitry. The video processing functions of subsystem 34j can be implemented only on the combined signal, as opposed to each individual component signal corresponding to each individual video input source.

Figure 6:
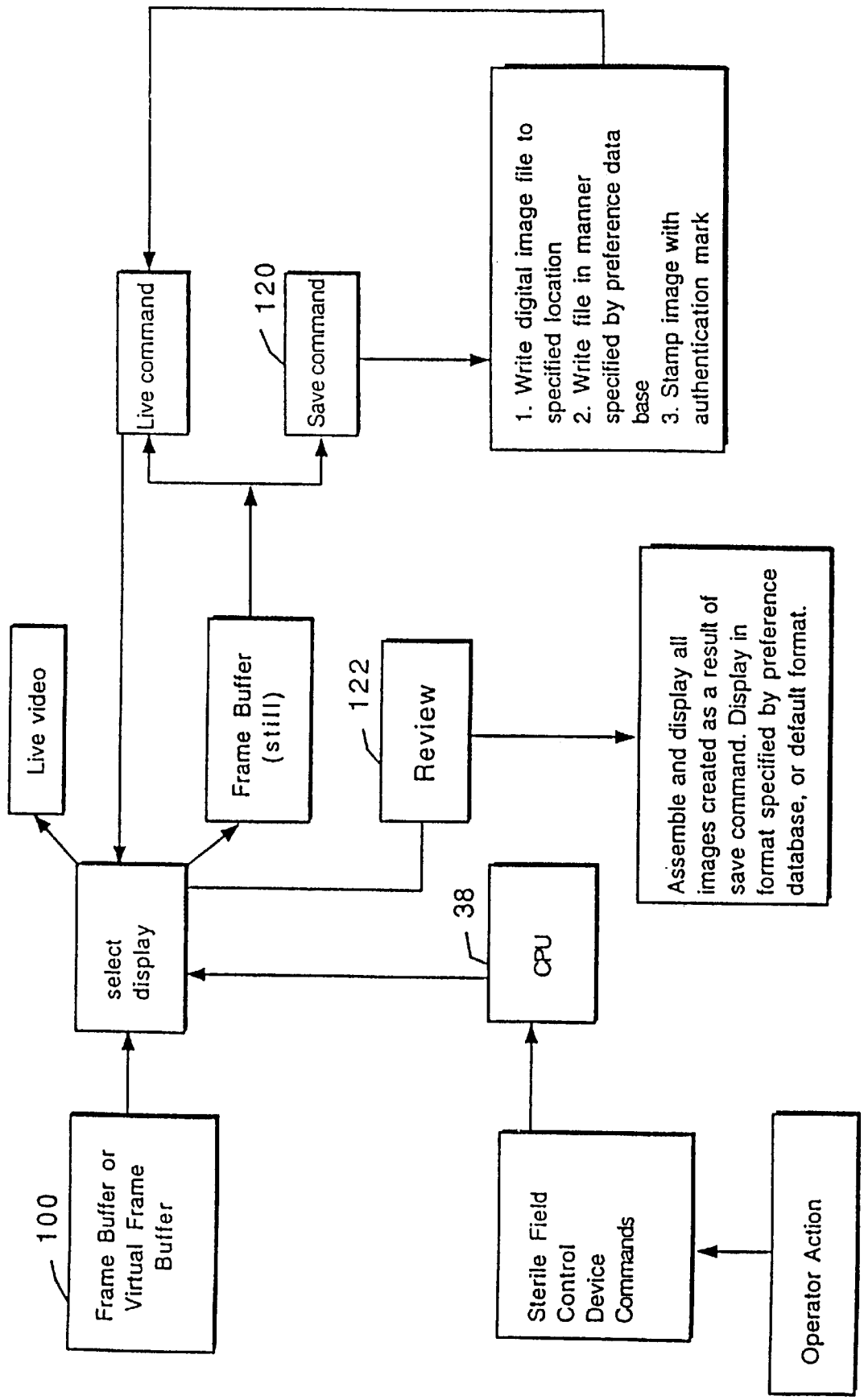
FIG. 6 illustrates a procedure for capturing and storing images in the system of FIG. 1.

Referring to FIG. 6, another function performed by video subsystem 34j is capturing images from frame buffer 100 (FIG. 4) and storing the images in memory.

Capture can occur by direct operator interactions (via, e.g., remote control 48 or a pointing device). A single button press can take a snapshot of the current information on the screen and transfer it to a memory media as a digital file. This system provides additional logic to allow toggle between "freeze" and "live," until the desired image is frozen. The image can then be saved to memory, by executing save command 120. Thus, the surgeon can elect to save or discard any image.

The freeze and capture functions can be controlled by any data input device 22. One implementation allows control by hardwired buttons on the camera 44 or infra-red handheld remote control 48. The review function 122 displays all images captured, either as a composite of many postage stamp size images, or as a sequence of full size images. This allows the operator to be sure adequate images have been captured.

The system allows the user to view all acquired images that are related to a specified procedure. The images are viewed as an array of images, reduced in size to allow several images to be viewed on a single screen.

The multi-image viewing function allows the operator to review acquired images during or after the procedure to verify that adequate images have been obtained. During a procedure, the review function is accessed by a keypress, infrared remote control signal, or camera button function. All images acquired during the active, or relevant case are displayed in an array of multiple images on a single screen. The maximum number of images per screen and the size and location of the image display are designated in the program setup and user preference database 20. Additional pages or screens of images are added to allow review of all acquired images when the number of acquired images exceeds the maximum number of image display locations specified for the review screen. The user can page forward and backward through the acquired images. Another operator signal causes the system to return to the live video acquisition mode or exit the acquisition mode.

Thus, the system allows the user to rapidly review all images stored during a procedure prior to completion of the procedure. The system provides for rapid alternation between a page of "postage stamp" miniature representations of stored images acquired during the current procedure and live image acquisition.

After a procedure, images acquired are presented in a similar multiple image per screen display manner. Images can be selected from all available images using the database query mechanism, or by relationship to any criteria specified by the user, or other programs employed by the user. When used in this mode, a function is provided to allow the user to select an individual image from the multi-image format display. After selection, the designated image is displayed at full screen scale and size. At this time, the user is presented with additional options for image manipulation, printing, annotating (adding text to the image), moving or copying the image to another location or file, or deleting the image.

The speed of transfer of images is important, as is the simultaneous creation of a postage stamp size image to be used later for the review function and an image library browse function (described below).

The frame buffer is transferred to a designated set of pages in memory as planar pixels (one plane each of red, green and blue). All operations on the pixels are performed in RAM. The postage stamp image is subsampled by a rapid scheme that only performs the dual writes of designated pixels with minimal CPU time. Disk write, which is the slowest of the functions, is performed by block writes, which are the fastest way to do this.

The review function works as follows: When the command to review is issued, the system looks at the current image directory and prepares space for one postage stamp per image in the directory. The system pulls up the postage stamps and loads them to memory by reading the designated part of the image file by offset so that no calculation or reading other than the image is required. The layout of the postage stamps for display is specified by a form. This makes it fast. Once the page is configured in memory, it is transferred to the display device. The review function operates quickly, thereby allowing surgeon to see what's already in memory, which is an important feature of the system.

The same method is used to display images in the library browser function, but in the browser function, the image itself is used as a button that, when activated, results in display of the full screen version of the image associated with the postage stamp.

The size of the postage stamp size images and the layout of the browsing screen can be set by preference. In one embodiment, it is 3 rows of 4 image each. When the number of images stored exceeds 12, additional pages are composed and displayed 12 images at a time.

Figure 7:
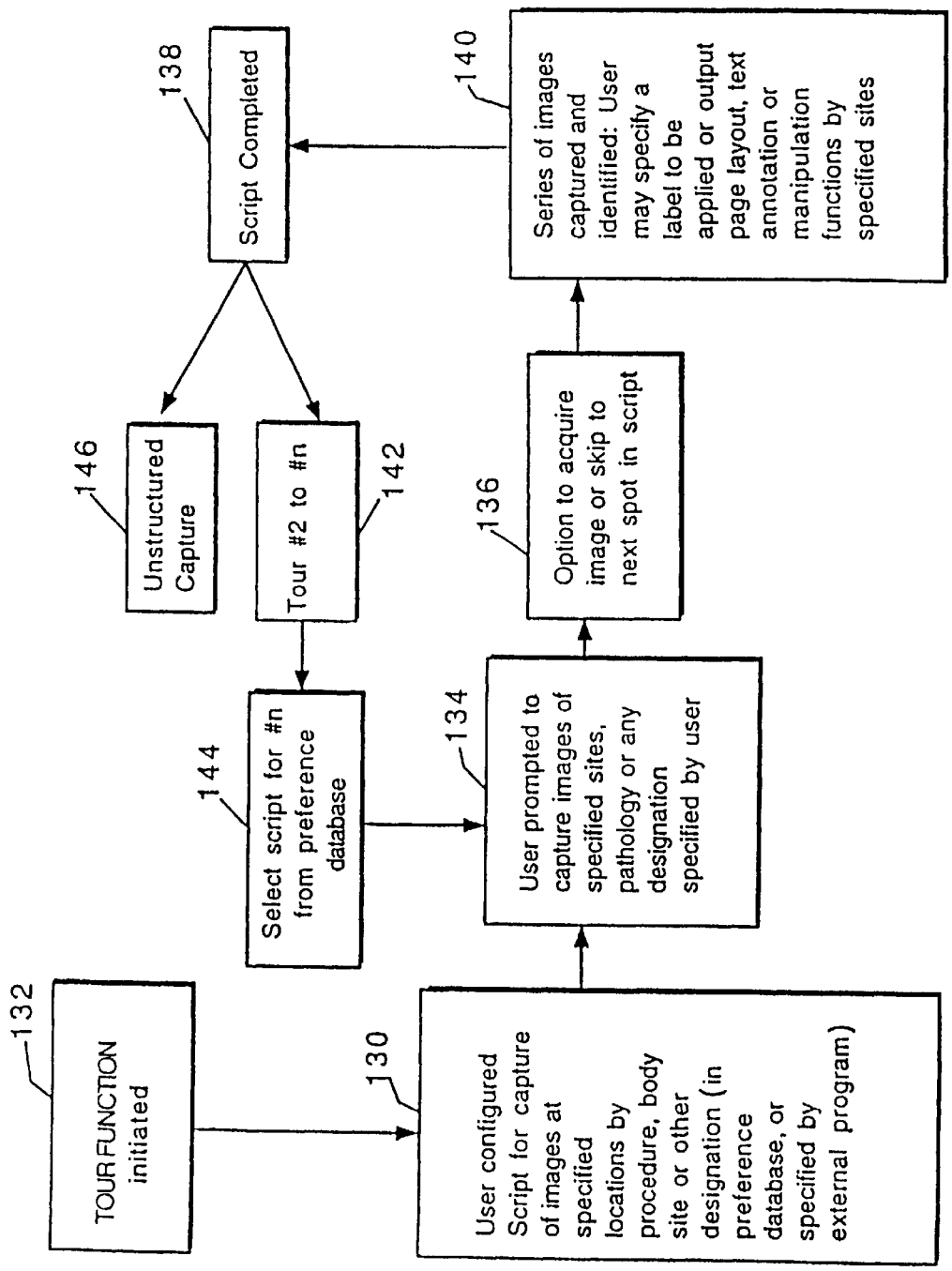
FIG. 7 shows a "tour" procedure for capturing images in the system of FIG. 1 according to a predefined script.

FIG. 7 illustrates a "tour" function performed by system 10. Preference database 20 contains, for each physician who uses system 10, one or more "scripts" 130 for designated captures of images. When the tour function is initiated (132), system 10 prompts the physician (134) to capture images by anatomic site, pathology or other designation. Prompting is performed via a graphical object or a text clue imposed on the displayed image that guides the operator to the proper position for capture. The physician has the opportunity to skip an image or acquire additional images during the tour (136). Upon the completion (138) of the script, system 10 has captured and identified a series of images (140) specified in the script.

Multiple tours, i.e., pre-op and post-op tours can be designated (142). Pre-op and post-op tours advantageously show pathology and post endoscopic procedure results or status. If multiple tours are specified, system 10 selects (144) the scripts for the tours from preference database 20 in a logical sequence that corresponds to the natural flow of the surgical procedure. The format of the printed output may identify the sites as pre- and post-intervention.

A special case of tour is invoked when images acquired at different times during a procedure are to be displayed on a single tour print format. In this instance, it is desirable to interrupt or resume a given tour. When a tour is configured such that it can be interrupted, sequential "start tour" commands will cycle through available tour scripts. For example, 3 tours can be attached to a given form, and designated as interruptable. The first start tour command will initiate tour script #1, a second keypress advances to script #2, a third to #3, and a fourth start tour command returns to script #1. If an image is present for a given prompt in the tour script, it is displayed to the screen. At this time, the user presses "skip" to advance to the next prompt, or "capture" to return to live video, discard the image associated with that prompt, and re-capture an image to be associated with the prompt. Alternatively, the user can specify that re-activation of an incomplete tour will stop only at prompts that do not already reference an associated capture image.

The available tour scripts are related to the form in use when the tour function is initiated. The printed output of the tour and its labeling are specified by the output format file called by the tour. The combination of the system prompts to the user and the logic used to prepare the tour script are what give the system the ability to infer something about the content of the image for use in the tour formats where text labels, stock images and layouts are added to the images without further user intervention.

Figure 8:
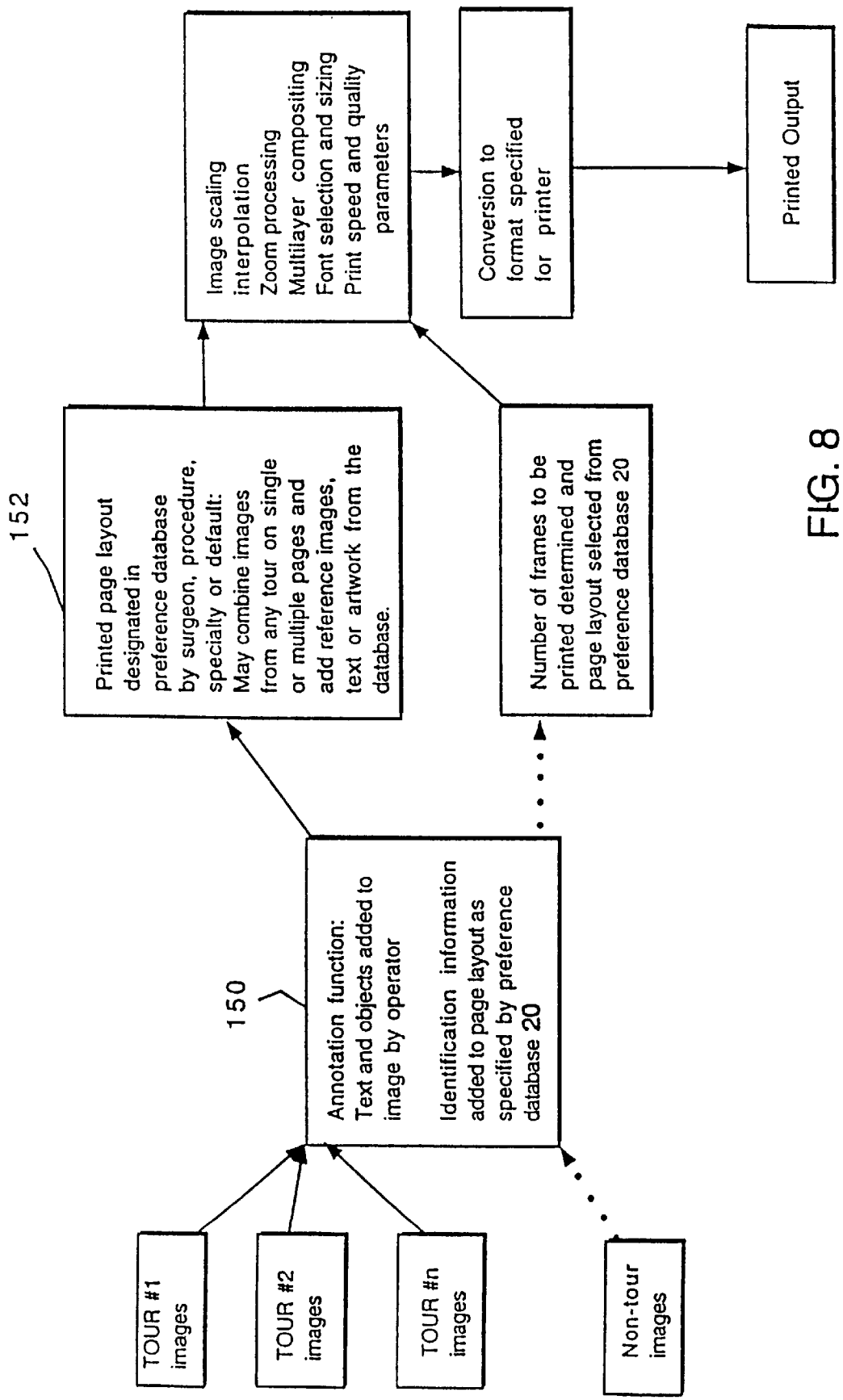
FIG. 8 is useful in understanding how the system of FIG. 1 formats printed outputs of images.

Referring also to FIG. 8, the tour function also includes automatic annotation (150) of images obtained in each tour with predefined text or graphical information. The tour can also specify composition of printed or other output, combining acquired images and/or stock images or diagrams that lend clarity and context to the images acquired (step 152). Page formatting allows multiple images in multiple sizes to appear on a single page or on multiple pages.

Printed page layouts can be defined and modified based on a taxonomy defined when the user defines the functions of tour. In one embodiment, the page description language is post-script level 2, but other interpreters for conversion to other file formats can be added. The tour mode script will define how images captured in the tour mode will be sized, scaled, displayed, arranged, formatted and labeled. Images captured in the tour mode will define how they will be displayed, arranged and labeled. Additional drawings, diagrams, or stock images can be pulled into the defined page layout. Once defined, the layout can be stored, or printed to hard copy or slides.

Images captured randomly (outside of a defined tour) in an unstructured capture (step 146 in FIG. 7) are formatted by a user-defined algorithm, or a default format is used in the absence of user instructions to the contrary. This layout formats pages to conform to a predetermined optimum number of images and spatial arrangement based on the target printing or display device specified in the user preference (as set forth in preference database 20). In addition, the user has the option to select the maximum number of images to be displayed on a page on the selected device. The selection can be made at the time of printing. In the event no selection is made, the system will use the default format specified in the preference database. In all cases, image size, scale and position will be automatically calculated by the system prior to printing.

Unstructured captures are printed in a manner such that they are visually pleasing and occupy the maximum imaging area available on the target output device. These calculations are performed at the time of output, and are specific to the capability of the target printing device. Video printers are known that will print ¼ of a page if the 4 picture per page mode is set if only one image is in memory. In the present system, in contrast, the image print format is selected based on the number of prints to be printed, up to the maximum per page specified by the user preference.

In a session in which both tour images and random images are acquired, a page layout for the prints will be generated consisting of a tour format plus a random format based on desired output device. The user can configure and modify the layout at any time. If no user selection is made, a default layout is used.

Figure 9:
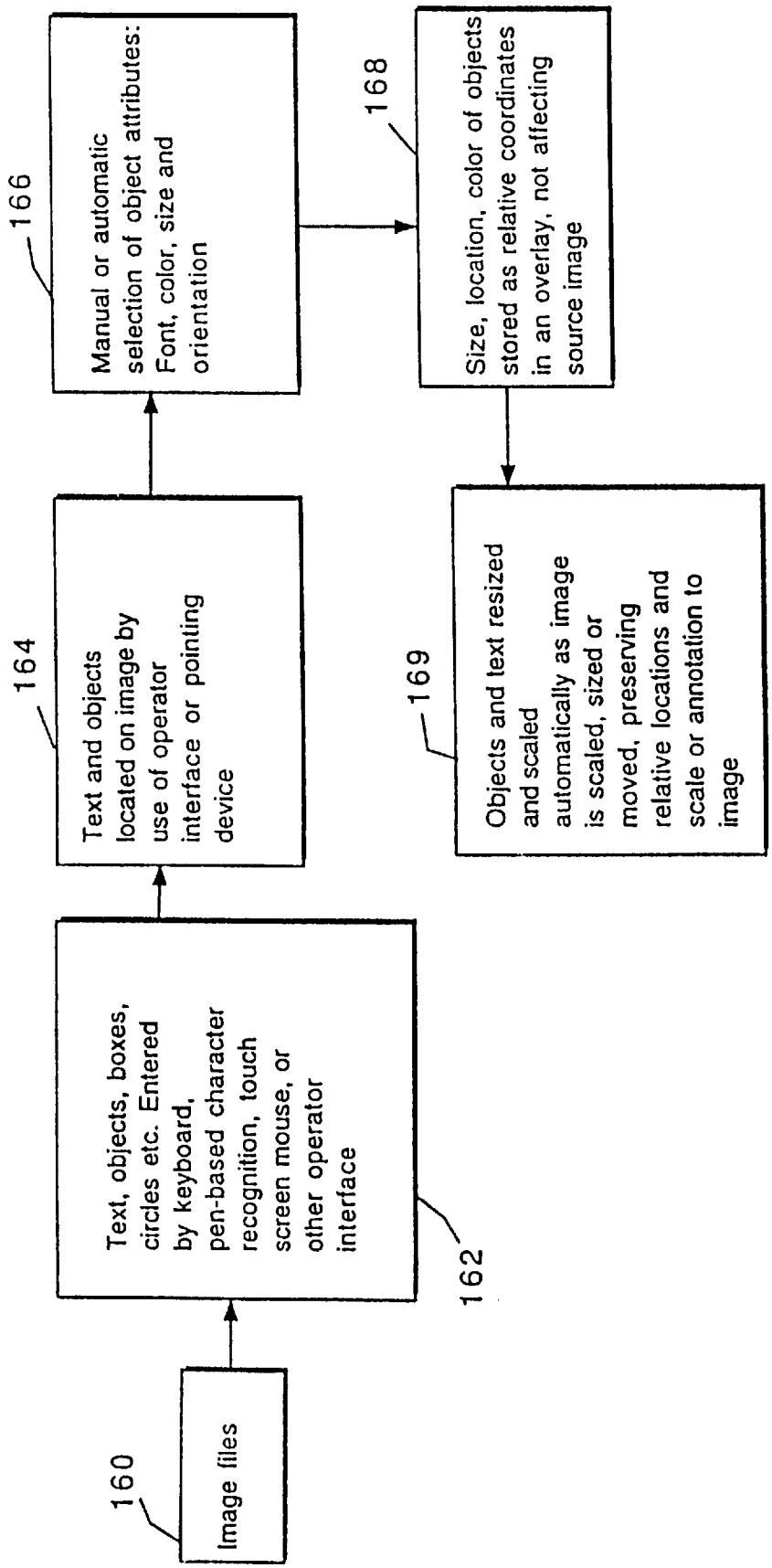
FIG. 9 illustrates a procedure for annotating images obtained by the system of FIG. 1 with text and graphics.

Referring to FIG. 9, system 10 also provides a simple technique for overlaying text or graphics on the acquired images (the technique can also be performed via a laptop or palmtop computer or other suitable computing device that is externally connected to personal computer 12). The resultant image is a composite of the annotation and overlay, so that the acquired image remains unchanged. The overlay text is anti-aliased for improved appearance. Anti-aliased text is used extensively throughout the interactions with the system. The anti-aliased text uses broadcast standard anti-aliasing technology in which text and background colors are manipulated on a pixel by pixel basis to give the illusion of smooth transition and well-defined text borders even while the system is operating in the RS170 display standards.

Thus, the system formats acquired images to improve the communicating value of the images. Communicating value is enhanced by combination of the images with text information from the database or with user-directed text information, and by formatting images into a printed array that may include backgrounds, previously stored images, text information, and sizing, scaling, or orientation operations. The formatting functions are automated based on user-defined or specialty-defined rules. Image formats are selected based on context, i.e., based on the script method described above, the procedure, or the identity of the user.

Text display by the system is performed in 2 modes: raster and outline. In raster anti-aliased text, a color map picture for each letter is used. Outline fonts are mathematical descriptions of the bounding lines of the text, and instructions to fill the inner portion of the text.

The use of anti-aliasing technology is important so that the text looks good on the interlaced screen.

The system provides the following important features of annotation:

1. The annotation does not damage the underlying image;
2. The annotation can be positioned using either a keyboard, a mouse, or other pointing device;
3. The starting point for annotation box location can be specified; in one embodiment, the starting point is in the center of the screen, which minimizes the distance the user needs to drag the text;
4. The color of the annotation (default is yellow with gray drop shadow) is selectable, but contrasts well with most endoscopic images;
5. Proportion and location of annotation is maintained when images are scaled for output.

Annotation generally starts at the image browser or library page. The desired image is selected by positioning the cursor around the desired postage stamp size image. The image file is then opened.

Starting with the image file 160, the operator (e.g., the physician) selects the text or graphical objects with which to annotate the image using one or more suitable data input devices 22 (FIGS. 1 and 2) (step 162). The input device is also used to locate the text or graphical object on the image (step 164). Object attributes such as font, color, and size can be selected manually or may be supplied by preference database 20 (step 166). The information that specifies the size, location, and other attributes of the graphical object are stored as relative coordinates in an overlay (step 168), and thus do not affect the source image. Finally, the objects and text are resized as the image is scaled for display (step 169). Printed output of the image/overlay composite will appear as if the overlay were part of the image itself.

Annotation can be performed in a similar manner at both the image and page layout levels. A single image or page layout can possess multiple annotation overlays. Single or multiple overlays may be presented as a composite with the image. The overlay may also possess the attribute of translucency, ranging from obliteration of the underlying image to transparency in areas in which the overlay is not visible. Thus, the annotation can be partly transparent. Single or multiple overlays may be attached to an image at any time.

System 10 also displays system status and functions to the user in a format and style specified by the user. A CPU-directed digital video keyer 104 (FIG. 4) adds the status overlay to the video signal displayed by the system, in much the same manner as discussed above. The overlay includes text information, graphics, or other images. Thus, the system can use software intelligence to display the status of connected devices or the status of the system itself so that only important status information is displayed. The information is displayed in the way that is most useful to the operator.

Figure 10:
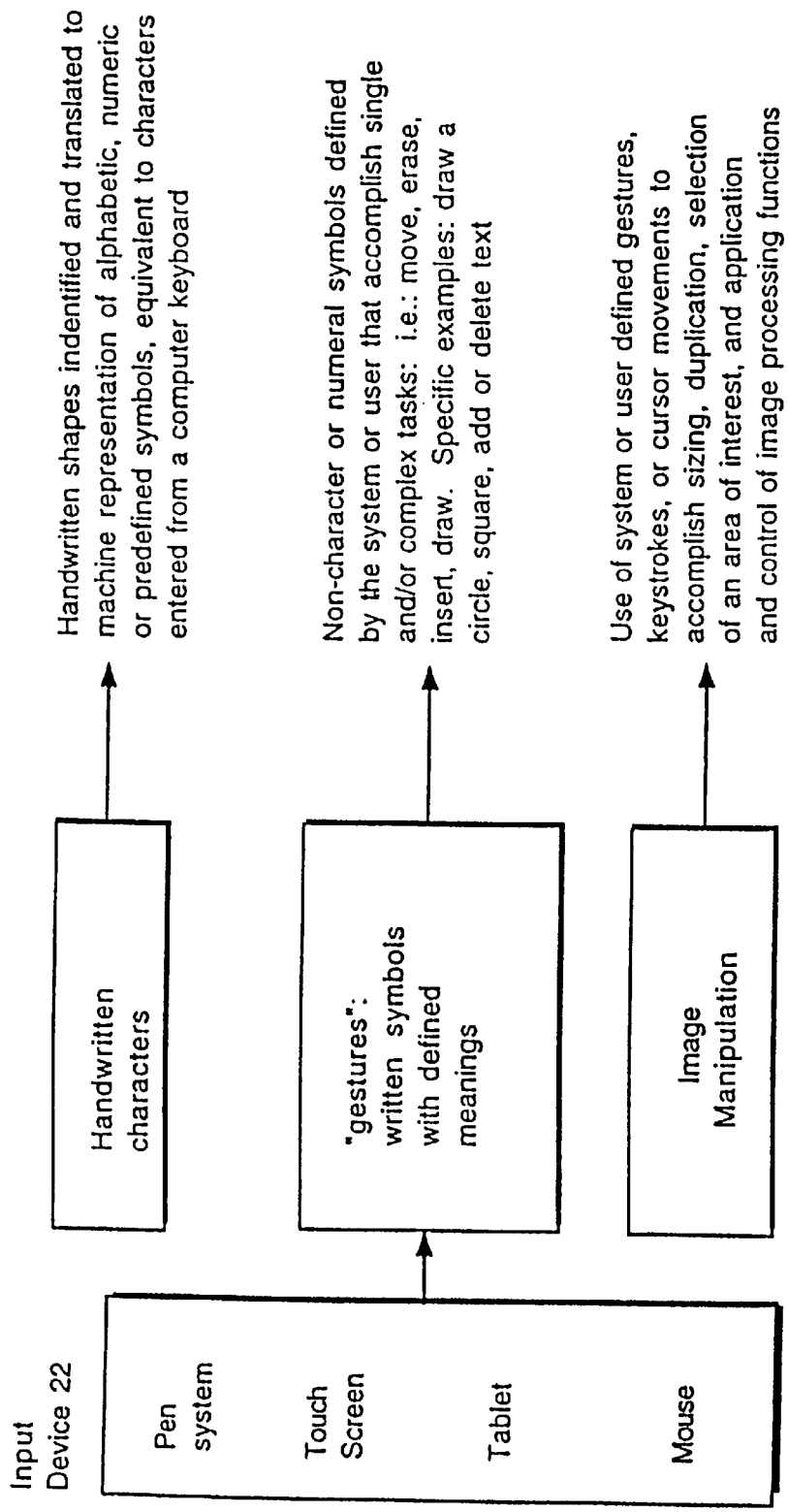
FIG. 10 is useful in understanding a character recognition feature of the system of FIG. 1.

FIG. 10 illustrates several different options available to the operator for entering the annotation information. An important functionality is "pen based" computing using a commercially available pen-based hardware 54 (FIG. 1) as the input device, but similar functionality may be obtained with other input devices. The endoscopic image is displayed, and the input device (e.g., the pen-based system) is used to annotate, manipulate, or process the image as discussed above. Using the pen-based system, the operator actually prints or writes on the screen, and system 10 translates the pen strokes into machine-readable characters. System 10 includes a search/shorthand capability to expand characters to an expected or defined word or most common "near hit."

The pen-based system also provides an extremely straightforward device for allowing the user to draw lines, squares, and circles, and for controlling area of interest processing and color.

As discussed above, annotations are stored as text and location so that when video formats are changed, or images are scaled to larger or smaller sizes, the aspect ratio, location, and contrast of the annotations with respect to the images are maintained.

As discussed in more detail below, system software 14 (FIG. 1) includes an image processing module or engine for enhancing the visual quality of images. Techniques implemented by software 14 include multiple methods for video noise reduction, masking, smoothing, sharpening, contrast and histogram adjustment, contrast stretch and contraction. Software 14 also analyzes the image and adjusts the algorithms to optimize the image based on predictable procedure, specialty, surgeon, or other predictive factors. Software 14 also uses multiple analyses of the source image to dynamically adjust the image processing parameters.

Image files created by system 10 are stamped with an internal "authentication" code not accessible to the user to designate the file as uncorrupted or structurally changed for legal purposes. Any image process that would substantially alter the information contained in the file causes this stamp (dirty bit) to be modified, thereby indicating that the file is no longer primary source documentation. The utilities provided to cause image modification provide an opportunity to copy the image prior to modification so that alterations can be performed without compromising the evidentially quality of the documentation.

Figure 11:
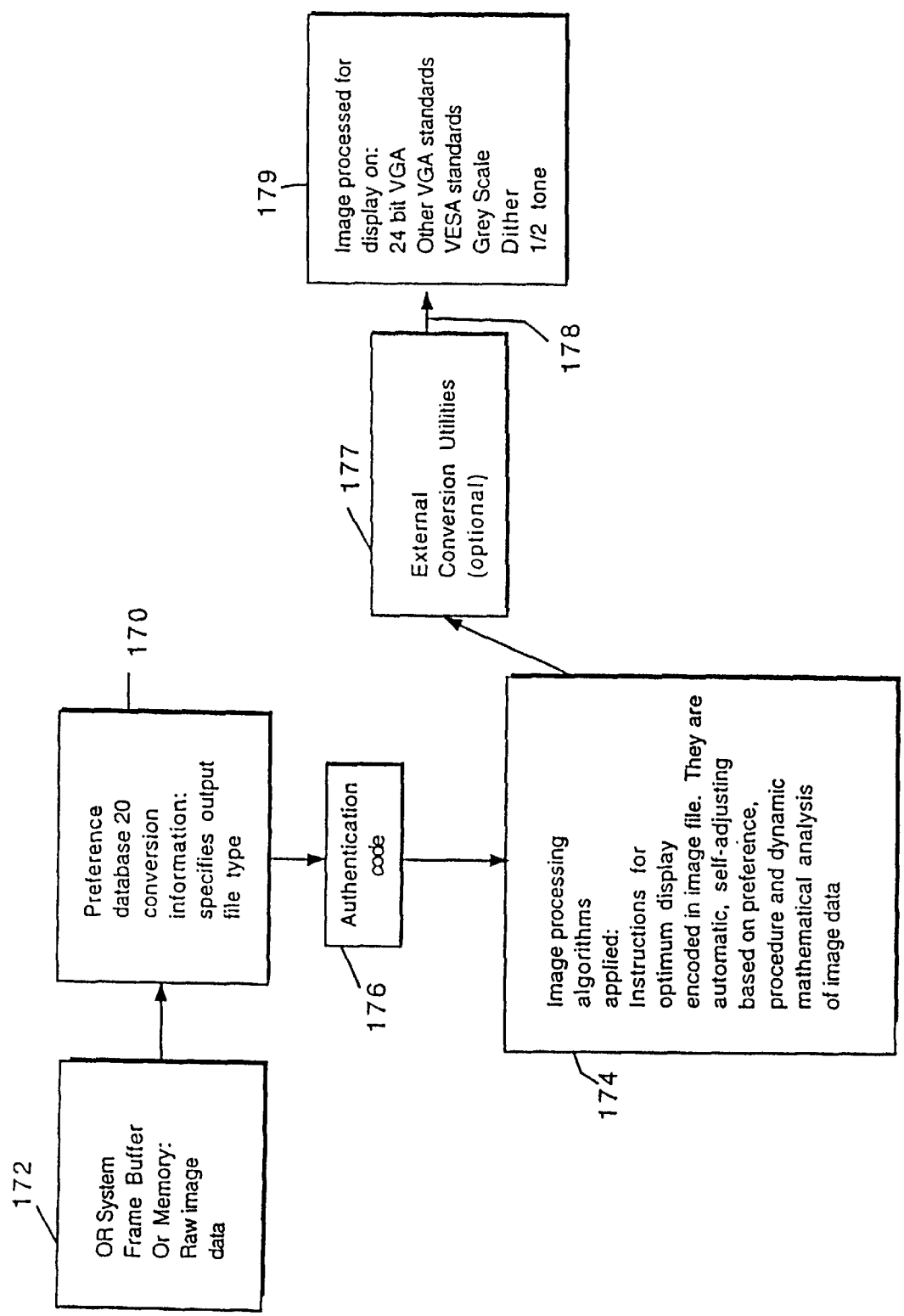
FIG. 11 shows a procedure implemented by the system of FIG. 1 to convert the video format of an input image to a different video format for use by an output device.

Referring to FIG. 11, as discussed above, video subsystem 34j processes images obtained during endoscopy for display on virtually any type of display device and in any suitable format. Preference database 20 supplies the conversion information that specifies the file type of the output image and the process to be performed (step 170). Video subsystem 34j uses this information to process the raw image data 172 (step 174). It is immediately prior to this point that the authentication code is applied to the image file (step 176). If desired, external conversion utilities are applied to the image file (step 177). The image output file 178 is then processed for display (step 179) in any of the formats listed in FIG. 11. Processing occurs via a process of color reduction, whereby in the transition from a high (e.g., 24) bit depth to a lower bit depth (e.g., 16, 8, or gray scale), the process is one of calculated selection of specific color representations to be retained (as opposed to arbitrary file truncation). The color reduction technique is based on commonly used algorithms including frequency and domain calculation. The available palette of colors is used to best represent the colors present in the source image. Processing occurs via a process of color reduction, whereby in the transition from a high (e.g., 24) bit to a lower bit depth (e.g., 16, 8 or gray scale), the process is one of calculated selection of a specific color palette to best represent the color fidelity of the source image, as opposed to arbitrary file truncation.

Referring again to FIG. 2, controls of a VCR 66 are programmable using one or more data input devices 22 (e.g., remote control 48). Signals from remote control 48 are interpreted by a command interpreter in remote control adapter 34c according to preferences stored in database 20 that associate actions taken by remote control 48, such as the actuation of one or more buttons on the device, with a command. The command interpreter relays the appropriate command (e.g., for record, stop, pause and play) to VCR subsystem 34m, which in turn transmits the commands to VCR 66, either via a hardwired connection or via interpreted and generated infra-red signals.

In the hardwired implementation, the handheld infrared signal is processed by the receiver. A code is reported to CPU 38 via bus 36, and CPU 38 dispatches a command from the device driver specified in the database to the end device, in this case, a VCR. The command is dispatched via an RS232 interface, or a device-specific interface. In the RS232 implementation, the device may return an acknowledgment or error response that is interpreted and processed by the CPU. In all cases, the device driver contains the logic and rules for interpretation, such that the command processor and CPU interact with controlled and control devices in a consistent and standard manner.

The invention supports the use of an internally mounted super-8 format, S-video recording apparatus. This apparatus is supported as follows: The system utilizes high quality video-8 and high-8 standard miniature video tapes. The operation of the system (record, play, tape motion and power) are controlled by an interface to the CPU, as a subsystem. Tape counter information related to the relative position of the tape is communicated to the system database. User commands are issued to the device using any of the system-supported control interfaces described hereinafter. When a user issues a record command, the system actuates the video recorder for a specified number of seconds. The system indicates the record operation to the user via a screen or audio signal. An icon representing the video clip is saved in the image browser. An audio annotation file describing the video clip or a text description of the information in the video clip can be associated with the icon. The icon itself contains the tape counter address of the clip. The system can issue commands to the tape device to queue the device to play the designated segment of the video tape.

In the infrared implementation, the handheld infrared transmitter 48 generates a signal that is handled in two possible manners: 1) the target device directly receives, interprets and responds to the infrared emission of the handheld device, or 2) the system infrared receiver interprets the infrared emission of the handheld unit, and then sends a command to another infrared emitter to emit an infrared signal that can be interpreted by the target device. In the first case, the handheld unit contains memory for codes to produce the correct infrared signal, or sequence of signals. In the second case, the database contains a taxonomy of the signals, and rules for selection of signals. In this way, the system remains generic, and able to support a wide variety of devices. In addition, user-specific definitions can be applied to the rules for selection of signals such that the same keypress may result in different operations of the target device. Such preferences are stored in the preference database.

A provision is also made for support of a system in which frame-by-frame address information is written onto the video tape. Frame addresses are stored in the imaging system database, and can be used to index, record, and playback videotape on a frame-accurate basis. Frame-accurate code is applied to the videotape by one of several commercially available personal computer interfaces. The interface reports time codes to the host computer, while simultaneously recording the frame information on a special track on the video tape. The host computer relates the frame numbering information to the database. Later, the host computer retrieves the frame information, and issues a command to the VCR control interface. The interface is capable of controlling all functions of the VCR with frame-by-frame accuracy in response to commands issued by the host computer. A typical command interaction would be as follows: The host issues a search command, and reports a frame number retrieved from the database. The interface causes the VCR to read the special track of the information, and advances the tape to the desired frame, where the VCR pauses, waiting for the next command. A "ready" response is returned to the CPU via the interface, and the next command is issued.

System 10 is also capable of interactive recording or playback of audio signals. The audio material is written to and played back from digital files by an audio adapter subsystem 34 (not separately shown in FIG. 2).

Figure 12:
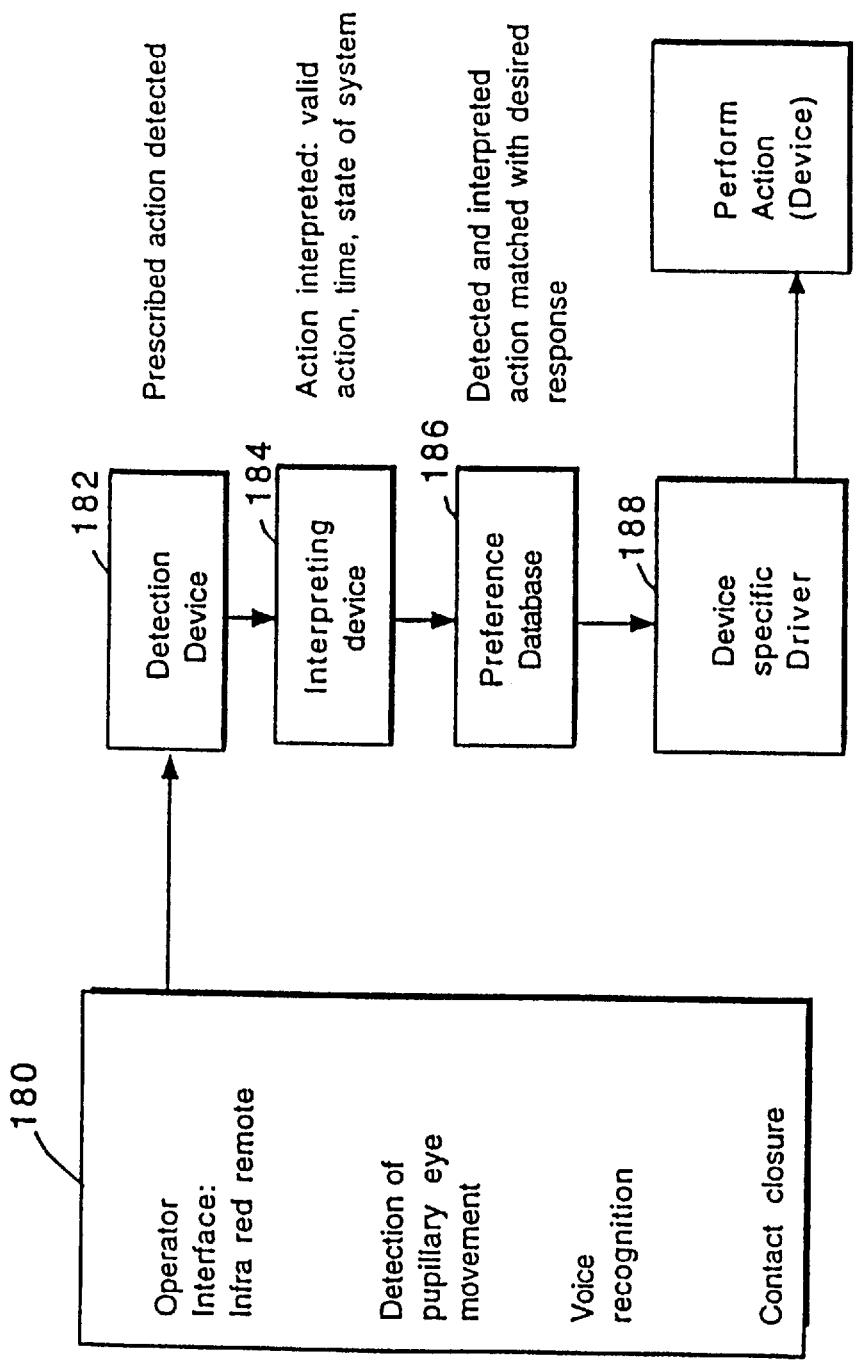
FIG. 12 is useful in understanding the operation of a remote control feature of the system of FIG. 1.

Referring also to FIG. 12, the operation of system 10 in response to the remote control devices that can be used with the system is shown. As discussed, the remote control devices include infrared remote control 48 and voice pickup 50. Other remote control techniques, such as detection of pupillary eye movement or the closure of contacts on, e.g., a footswitch, may also be used.

Voice pickup 50 enables the operator to perform spoken actions. The spoken speech is processed by a voice activation subsystem. The speech input is compared to the preference database taxonomy, and the appropriate action is communicated to the target device impacted by the command.

Thus, actions taken by the operator can include speaking, pressing a button, contact closure, or other actions.

In response to an action taken by the operator, such as the depression of a button on IR remote control 48 (step 180), the subsystem 34 associated with the device (in this example, remote control adapter 34c) detects the signal (step 182) and interprets the signal (step 184) using information stored in an internal memory (not shown). Subsystem 34c then accesses preference database 20 (step 186) to determine the action to take in response to the operator's command. The action is communicated to the device driver for the device that is impacted by the command (step 188), and the action is performed. Thus, a generic action taken by the operator is translated to a device-specific instruction according to the preferences of the particular operator stored in preference database 20.

The same action can result in different commands or actions depending on when in the procedure the action is taken, or what procedure is in effect at the time. The taxonomy of responses and logic for response selection is stored in the preference database. The commands are issued and received as generic commands, and then interpreted by the software of the system based on the rules specified by the preference database. The responses are governed by identity of the user, the procedure, or other information input into the system. Additional functions can be added, using a minimal number of controls at any given time. Because the selections will be relevant to the context of the job at hand, the functions presented to the user will be the smallest sub-set of all system functions required to complete the given task at hand. In addition, the actual operation of the functions can be adjusted such that the increments of the response will be tailored to the expected range of operation in a given circumstance. For example, in a procedure in which large differences in brightness are anticipated, the incremental response to a single brightness increase command is greater than the incremental response to the same brightness increase command issued during a procedure in which smaller differences in brightness are anticipated. Further, within a single operation, the sensitivity of increase is dynamically, or ballistically, compensated. Issuance of multiple repetitive commands results in increasing incremental change. In this way the system is both rapid in response, and sufficiently accurate in response.

The system integrates and distributes commands to the appropriate subsystem. I.e., one or many mechanisms to capture operator desires can communicate to one or more subsystems.

The available input devices can include keyboard, mouse, hardwired and wireless remote control, speech recognition, and handwriting "pen based" devices. The input devices accept generic commands such as keypress, switch closure, or receipt of an infra-red signal. The input handling engine of the interface compares the generic input of the control device, matches it to the action specified by the user preference database (described below) and issues the correct command to perform the action or response specified in the preference database. In this way, the same generic action can result in issuance of different commands based on the context of use, identity, or other characteristics of the user.

The database is structured to contain system-specific information, user preferences, patient text and image data. The user interface provides different and function-specific access to each of these database functions. System-specific information relates to available system resources and preferred configuration. This information is stored on the main system hard drive. Access to system-specific information is provided in a structured menu accessed by entering "setup" at the login screen. Setup is a reserved login ID, outside the normal end user operation of the system.

User preferences and identity, in contrast, are stored on removable media, and are accessible only after creating or logging into a user account by entry of an appropriate password. In this way, user preferences are specific to the user and portable between different locations or host machines. In the event that a user preference is not supported by a given host device, the host machine interface interprets the user preference and substitutes the closest available option that the host unit is capable of providing, or designates the preference selection as unavailable.

Creation of a new user requires specification of user login ID, password, secondary password, and specialty. Default configurations that can include video parameters, forms, and predefined image capture sequences are selected based on the predicted needs of the operator based on specialty. Operator-specific modifications can be performed at the time the database is created, or at a later time by editing the user preference database using tools provided by the user interface for that purpose. The function of logging on to the system, once a user is created, provides password security to user data and results in loading of user-specific setup parameters. A secondary password is provided to allow other personnel, such as nurses, access to preference and patient data records with a restricted set of permissions defined by the primary account holder.

Each removable media stands alone, and contains all information needed to initialize and load preferences of a user on any host system. When removable media is filled to capacity, the system provides a means to transfer user data to prepare new media. The system is independent of the identity of media, or specific media type. The only requirement for using media on the system is that the system contain the required hardware drive to support the specified media. No sequencing or labeling of media is required. As such, the host unit can read information entered by any system, as long as it is stored in the appropriate format on the disk. Similarly, data from the removable cartridges can also be utilized by database programs external to the system's database.

In one embodiment, the video subsystem provides the ability to optimize and enhance both live and still video image display based on available system resources and user preferences stored in the database. The video subsystem controls are executed by software commands issued to the video subsystem by a subsystem-specific software driver, under control of the main software engine. The functions of this portion of the invention relate to decoding and digitization of the incoming signal, processing the signal, acquiring digital image files and presenting them to the host interface, digital to analog conversion, and encoding of output video. Each step of the process is under software control mediated by device-specific drivers that implement the commands by sending control commands to the graphic processor, A/D and D/A converters and encoding or decoding chips, arithmetic logic units, or digital signal processor. Incoming video signals are decoded to RGB as required. In the RGB domain, functions are performed relating to managing the video input and output devices including adjustment of pixel clock rate, synchronization of video signals from multiple input sources, conversion of a variety of input signals to different output signals or resolutions, histogram operations on an image, contrast expansions, range and offset adjustments, overlay functions, combinations of video inputs, alternation between frame buffer storage of a given frame and continuous viewing of live video, magnification, scroll and pan functions, look up table conversions, frame averaging, frame doubling, and other functions. These functions are performed by a combination of a TMS 34010 graphic processor, an arithmetic logic unit, digital signal processor, analog-to-digital converters, digital-to-analog converters, or encoding or decoding chips as required. At output, the RGB signal then undergoes encoding required for the designated display device.

Enhancement of still images:

Stored images are enhanced by a user selection option for enhancement that implements a series of standard median, convolution, and contrast enhancement algorithms. Enhancement algorithms are run as monochrome algorithms on each of the red, green, and blue planes of the image where each pixel consists of an x,y coordinate and a value for the pixel at the coordinate. In one implementation, the color value is specified as an 8-bit value, although any value can be used. The routines to handle this are implemented by Signal Processing engine, (IGGY 360, described below). The first step in processing is to copy the image data into EMM. Image processing is performed in memory for speed. The original image file name is changed, so that the original image can be restored after the processing functions are completed. The algorithms are written as resolution independent. Resolution changes are handled by bi-directional interpolation. Linear interpolation can be used for speed, but bicubic interpolation is useful for quality. The preference database contains the exact sequence to be followed for the given instance of selecting the enhance features. The preference database also contains the information regarding the desired input and output resolutions, and parameters for each processing algorithm (e.g., sharpening factor for sharpening algorithm). These values are passed to IGGY 360 at the time the enhance selection is made.

The following example assumes a pixel value of 8 bits per red, green and blue value, for 24 bit color scheme. The image matrix is first interpolated to double the spatial resolution of the source image using bicubic interpolator 801. Next an auto crop function is performed. The maximum gray level (corresponding to black for the image) is traced radially outward from the central point of the image matrix until 5 consecutive pixels reflect an assigned maximum gray level (corresponding to black for the image). In this way the border around an image (which occurs, e.g., when one is using an arthroscope) is cropped from the image. If the border criteria is poorly defined (i.e., the edge is not detected) a bounding band for the crop is presented to the user for verification or modification using a pointing device. Image data outside the crop boundary is not modified, but is excluded from image distribution calculation and subsequent processing steps. Next, a distribution of the pixel values versus count is computed for each of the red, green, and blue component data matrices. In most cases, only a portion of the available range of 256 possible values is used. The values for the pixel values are remapped so that lowest pixel value is assigned the value of zero, and the highest pixel value 255, and each intervening pixel value distributed among the remaining values by multiplying the original pixel value by a ratio of V2−V1/V2, where V2 is the total range of the new distribution (Vmax−Vmin) and V1 is the total range of the original distribution (Vmax−Vmin). In this way the original pixel values are distributed across the maximum range possible for the system while preserving the same relative proportions of each pixel value to the total. Next, an appropriate sharpen convolution or median filter is applied to the data using the sharpen or filter parameter specified by the preference database. Sharpen and median (noise reduction) filters are standard algorithms based on a three pixel square (9 pixel) matrix used on each of the red green and blue monochrome images. In the sharpen filter, the values for the upper left and upper central pixels are multiplied by 50% of the value of the sharpen factor. The upper right corner pixel is multiplied by 100% of the value of the sharpen factor. The lower left pixel is multiplied by −100% of the sharpen factor, and the lower central and lower right pixels are multiplied by −50% of the sharpen factor. The left and right central pixels are not changed. The resultant value for all 9 pixels is summed, divided by 9, and the central pixel of the matrix is replaced with the resulting value. The process continues until all pixels are updated. For noise reduction, a similar matrix of 3 by 3 pixels (9 pixels) is used, replacing the central pixel of the tile with the median value, or the median value multiplied by a factor stored in the database.

The interlaced noise reduction filter reduces the motion artifact induced by interlaced acquisition of video. This filter reduces the "hounds tooth" appearance that results when motion occurs in the source image between the acquisition of the odd and even fields of video that comprise the frame. This filter results in superior correction of the artifact without the resolution loss inherent in frame doubling or frame averaging. The filter works by comparing monochrome pixels in the red green and blue planes. Pixels in scan line n and (n+2) are compared to the pixel value of scan line (n+1), starting with scan line 1. If the value of pixel in scan line (n+1) is more than (a) units (where (a) is a value specified in the preference database, specified as a=5 in one implementation) greater than the value of ((n)+(n+2))/2, (where (n) and (n+1) are the values of the associated pixel) then pixel (n+1) is replaced by the value of ((n)+(n+2))/2. If the difference between the calculated values is less than or equal to (a), then no action is taken. The result is that when significant differences exist between even and odd fields that comprise a frame of video, the difference will be minimized. When the difference is within the factor specified, no data will be altered. Again, this algorithm is implemented on a data matrix that has been doubled by using bicubic interpolation.

At completion of the specified chain of processing, the interpolator is called to scale the image to the desired display size. At completion of the processing, the image is transferred from memory to the display device or the disk memory.

Video Printer:

A video printer is operated as follows. The system generates a video signal that serves as the input for the video printer. The video signal is created by the system, as opposed to the live video signal produced by the video input source during surgery. The signal produced by the system can include image enhancement, annotation, and printing of multiple images on a single print.

The system generates control signals and receives control signals from the video printer via a serial connection. These signals can be used to replace the operator input normally required to generate multiple copies of multiple images.

Support of digital printing devices:

Printers capable of imaging and control via digital means can be controlled by serial, parallel, SCSI, GPIB, or other interfaces. In this instance, the system configures a file that consists of all raster data sufficient to produce the image, and device-specific digital commands to control the printing process. This information is passed to the printing device, and status is reported to the system via the interface connection. In this implementation, the invention performs all scaling, raster image processing, and color operations required to drive a printer that supports only raster data.

Post Script compatible devices:

Printers or devices containing raster image processors compatible with post script are handled as follows: The page description, control commands, and raw image data are downloaded to the printer via one of the above-described interfaces. The actual conversion of page description to raster data, including scaling, color correction, and other processes are handled by the raster image processor contained in the device. This configuration is much faster than the transmission of raster data to the connected device.

Interface operation: Heuristic process:

The system minimizes the number of options presented to the user at any given time. The system will select and present to the user the smallest subset of available system resources that is likely to be used for the job at hand. The selection process is based upon: 1) the resources currently available to the system; 2) the resources likely to be used at a given time; 3) identity of the user, or the procedure; and 4) the risk of inadvertent operation of the system during critical functions. The preference database contains the rules for operation of resource identification and allocation, so that the rules may be updated as system usage changes, or as new requirements or devices are added.

Available Resources:

The system will display only those options that pertain to features that are actually installed and operational. At system startup, and intermittently during operation of the system, a poll of available devices will be performed. Devices that are present and operational will be made available to the interface. Corresponding icons will display based on the likelihood that they will be used. Systems that respond with an error message will activate device-specific diagnostic routines to attempt to change the device to an operational mode, or will activate device-specific error handling messages. These error messages are ported to the user interface by changing the color of the affected icon to red, and by issuing a text error message that reports the identified fault. Issuance of the error report is prioritized based on the likelihood that the error will impede operation of the basic endoscopic functionality. For example, deficits in a video acquisition source will immediately flag the operator, and suspend further operation of the system. Non-critical deficits, for example, a printer for which paper has run out, will flag the user when the device is selected.

Context of Operation:

Only available options that are likely to be useful in the context of the current operational mode of the system will be presented at a given time. For example, during live video operation of the system, live video manipulation and image capture operations will be available. Options not likely to be used, such as printing or output selections, or options likely to suspend operation of live video, such as image processing, are not presented to the user.

Identity of the user:

Based on the user preference database, the user is presented with a user-defined subset of devices and functions. The available functions are a subset of all available functions and operations.

Two user sign-on passwords are provided. The preference database contains a table of authorities that determine which functions a user may access. Based on user training, and authorization, specific functions of the system may be restricted. For example, inexperienced users will have access to system initialization, or preparations for endoscopic operation, but will be denied access to potentially destructive operations such as image or record deletion.

Likelihood of Inadvertent Operation:

During live video operation, the user is presented with the most restricted subset of available features and operations. Most of the features presented relate to the operation of the real time image processing features. All features have an immediate escape, or return to live video operation. Errors that occur in an option selected from the live video mode are handled by return to display of live video mode, with a small annotation of the error at the top of the screen. Further operation of other options will be restricted until the condition causing the error is corrected.

Figure 14:
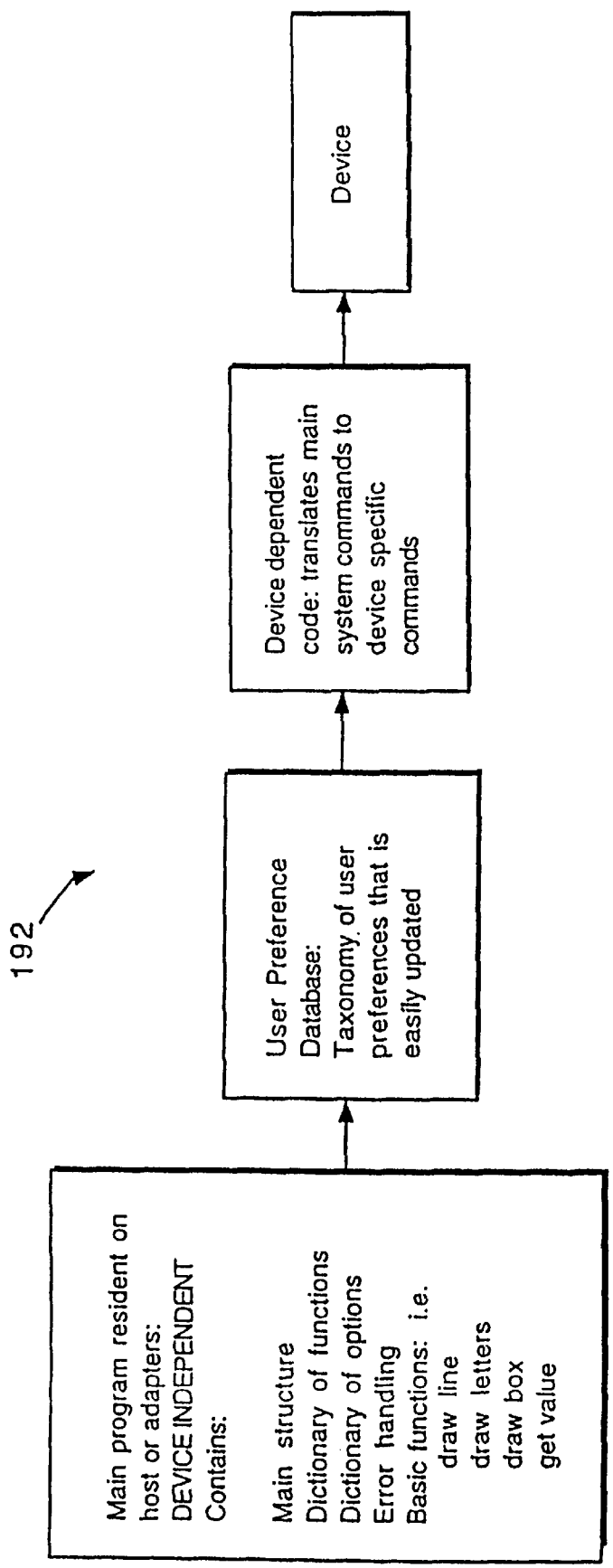
FIG. 14 shows the device handling architecture of the system of FIG. 1.

Referring to FIG. 14, the device handling architecture 192 implemented by system 10 is illustrated. This architecture allows many devices 16, 18, 22, 26 (FIG. 1) to be supported by a single operating program 14. Custom configurations are stored in a taxonomy in preference database 20, which is referenced during the configuration and operation of system 10. This architecture, and the structure and organization of the database (described below) allows system 10 to be platform and device independent—that is, when a device is added to or removed from the system, only the software driver that controls that device need be changed. Portions of the programs or device drivers may reside in host processor 30, the device itself, or on other media or memory accessible to host processor 30 and the device.

Figure 15:
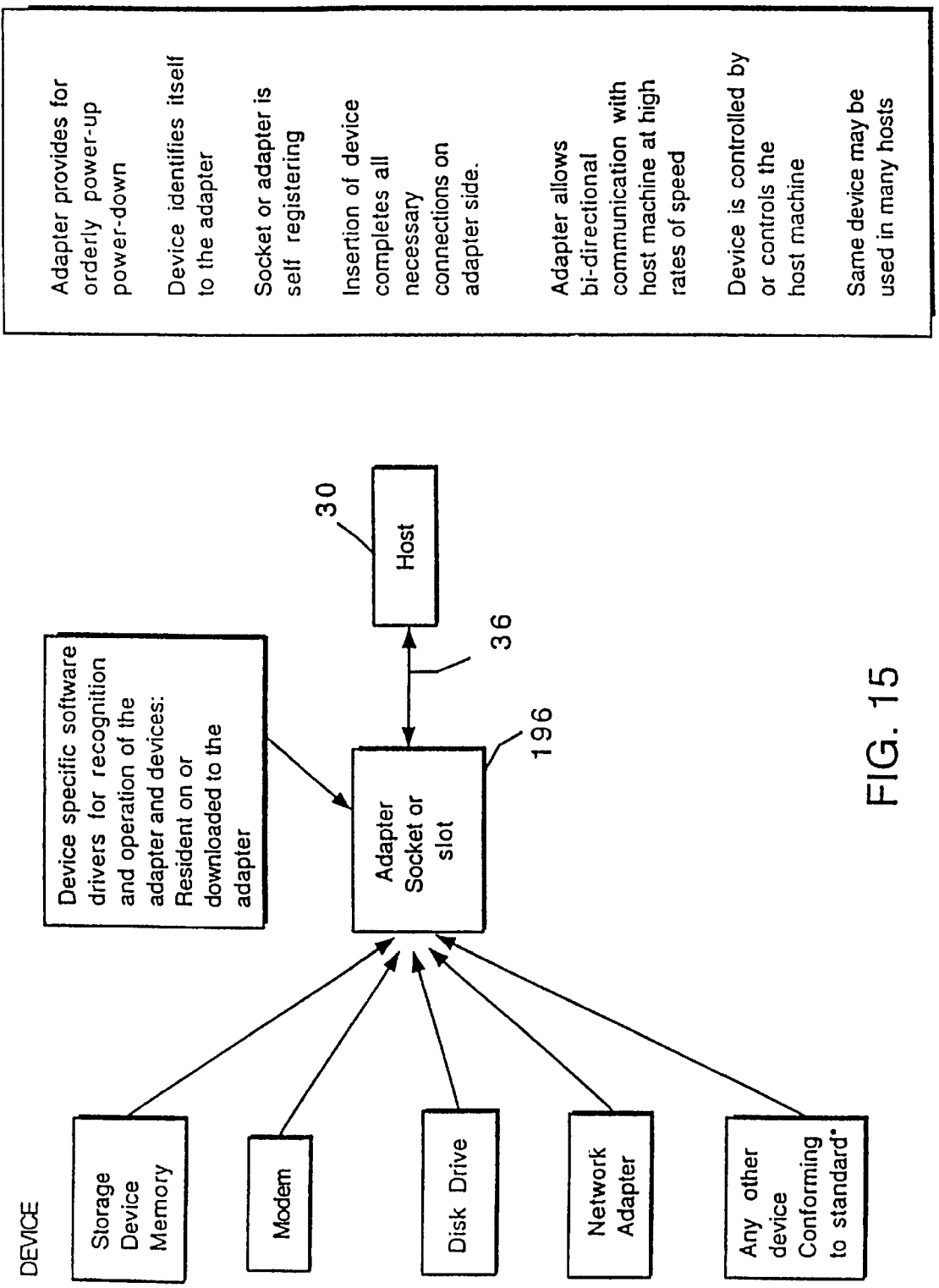
FIG. 15 illustrates the use of universal connectivity devices (that use, e.g., the PCMCIA standard) in the system of FIG. 1.

FIG. 15 illustrates the connectivity and operation of a PCMCIA adapter 196 (e.g., adapters 34f–34i and 34p of FIG. 2). PCMCIA is an evolving standard for an array of devices that include storage, communicating and other external functions. In system 10, the PCMCIA (or any other suitable standard, such as JEIDA) is used to interface to multiple input and output devices in a standard manner. PCMCIA adapter 196 is self-contained and durable, and is equipped with a standard edge connector for ease of use. No additional wiring is required; the adapter slot provides operating power. Thus, the action of inserting adapter card 196 into the slot in host processor 30 is all that is required to initiate appropriate identification and management of the device that is inserted.

A PCMCIA adapter 196 may alternatively be located externally to host processor 30. For example, a PCMCIA adapter 196 may be disposed in another device (such as a laptop or palmtop computer 54 (FIG. 2) that communicates with host processor 30).

Figure 16:
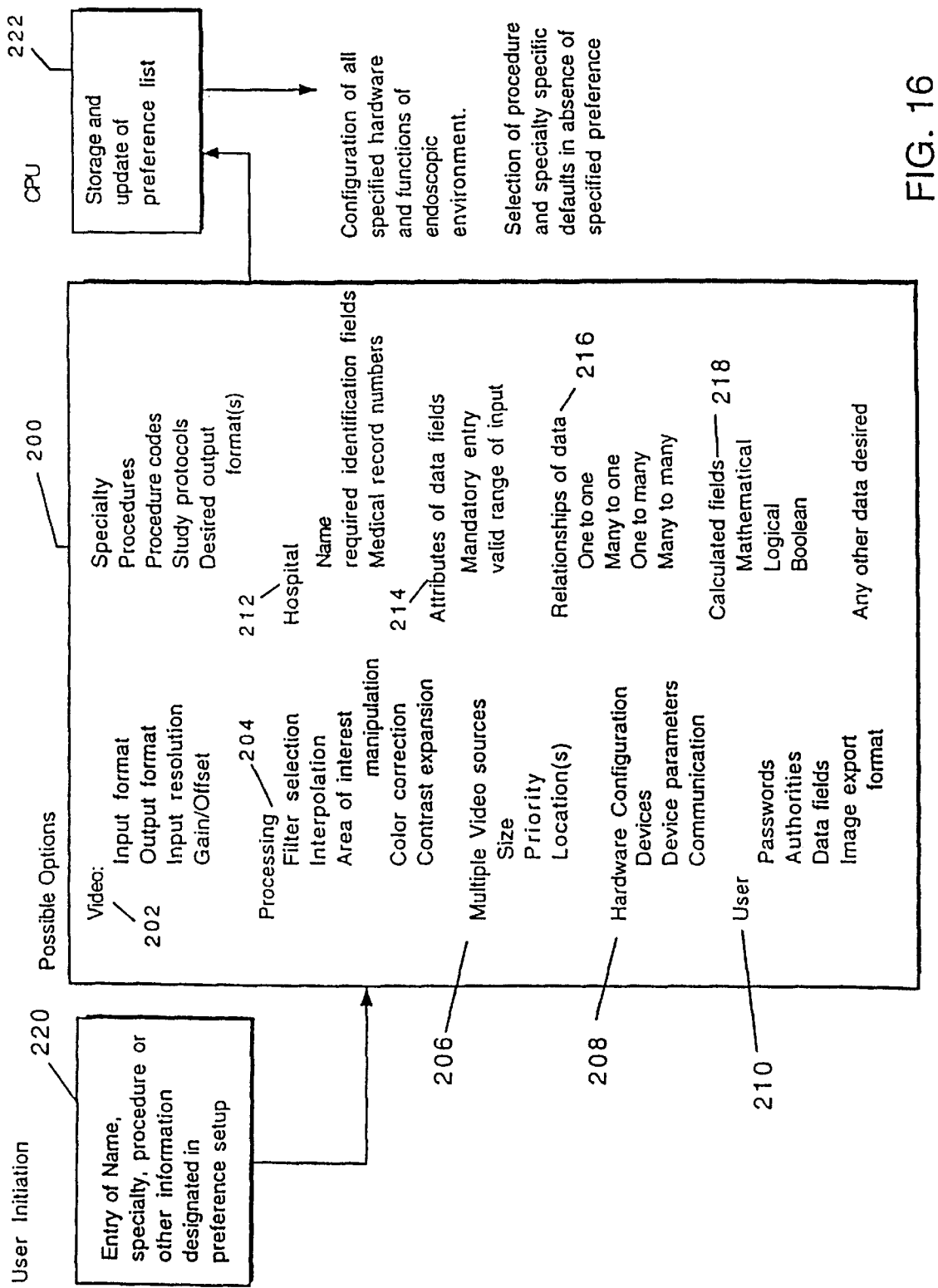
FIG. 16 is useful in understanding the operation of a preference database of the system of FIG. 1.

FIG. 16 illustrates options 200 provided to the user by preference database 20 and shows how the user and CPU 38 interact with preference database 20. Options 200 include specifications as to video format 202, processing 204, the video sources to be used 206, and the configuration of the hardware 208. In addition, information concerning the users 210 and the hospital 212 (or other facility in which system 10 resides) is also provided. The attributes of the stored data 214, relationships between the data 216 (e.g., one-to-one, one-to-many, many-to-one, and many-to-many) are also provided, as are calculated data field attributes 218, such as required entry, text, date, numeric, or decimal. Other types of data fields are date and time.

Different physicians who use system 10 typically have different preferences as to how endoscopy images are to be obtained, processed, stored, and displayed. Indeed, a given physician's preferences for these options may vary according to the procedure being performed, or even according to the particular stage of any one procedure. Preference database 20 classifies the preference information according to the individual physician, specialty, procedure, and stage of procedure to give the physician the capability of configuring and operating the devices in system 10 rapidly, according to his or her pre-stored preferences.

When the physician begins the procedure, the physician enters his or her name, specialty, and any other information that corresponds to the physician's desired setup, e.g., identification of the procedure to be performed (step 220). CPU 38 retrieves the preference information for this physician and procedure and uses it to configure the devices (e.g., cameras, CRT displays) preferentially used by the physician during the procedure (step 222). CPU 38 also maintains and updates the preference information in response to changes ordered by the physicians.

Figure 17:
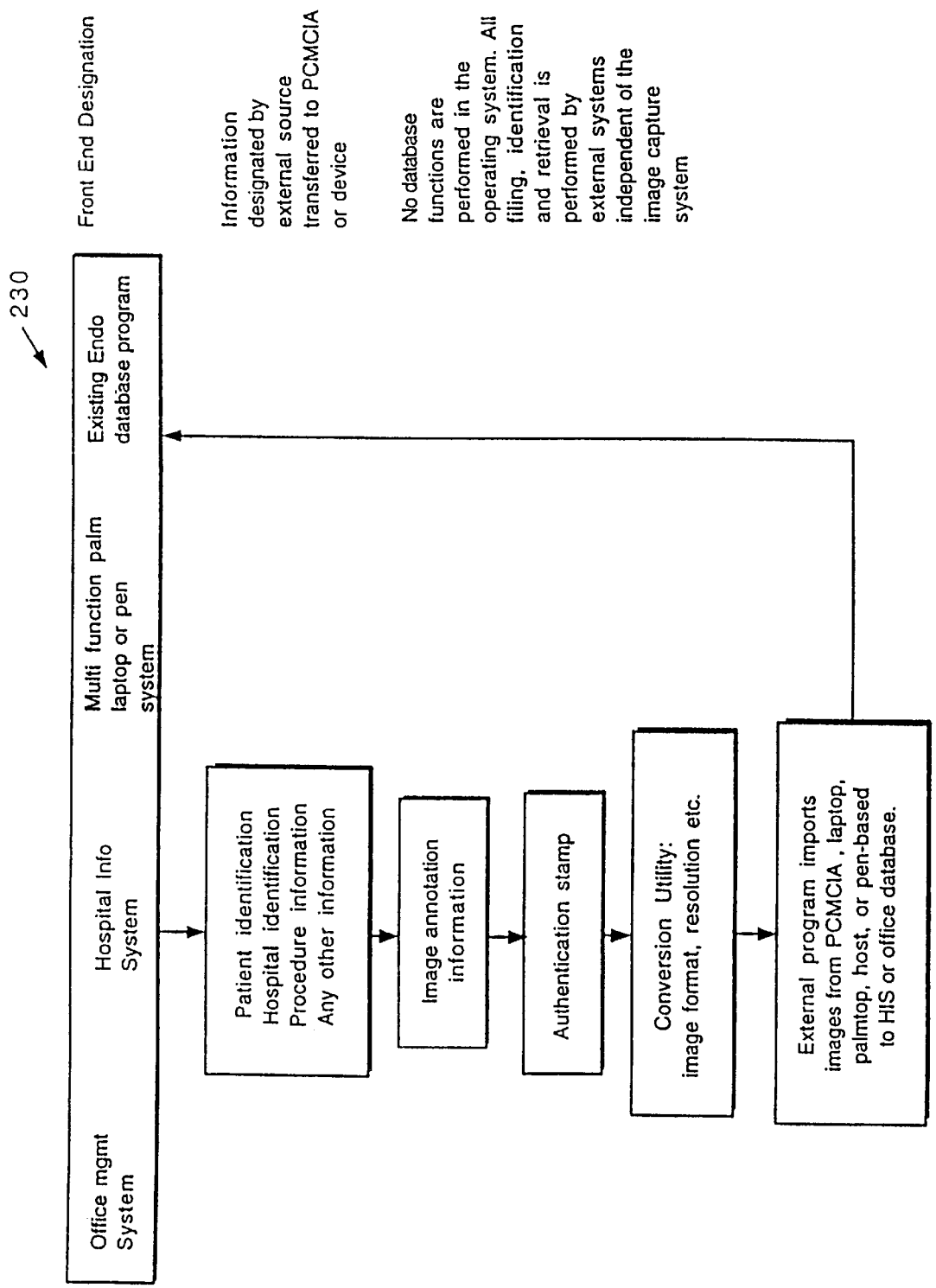
FIGS. 17 and 18 illustrate the storage of acquired images in an image database of the system of FIG. 1.
Figure 18:
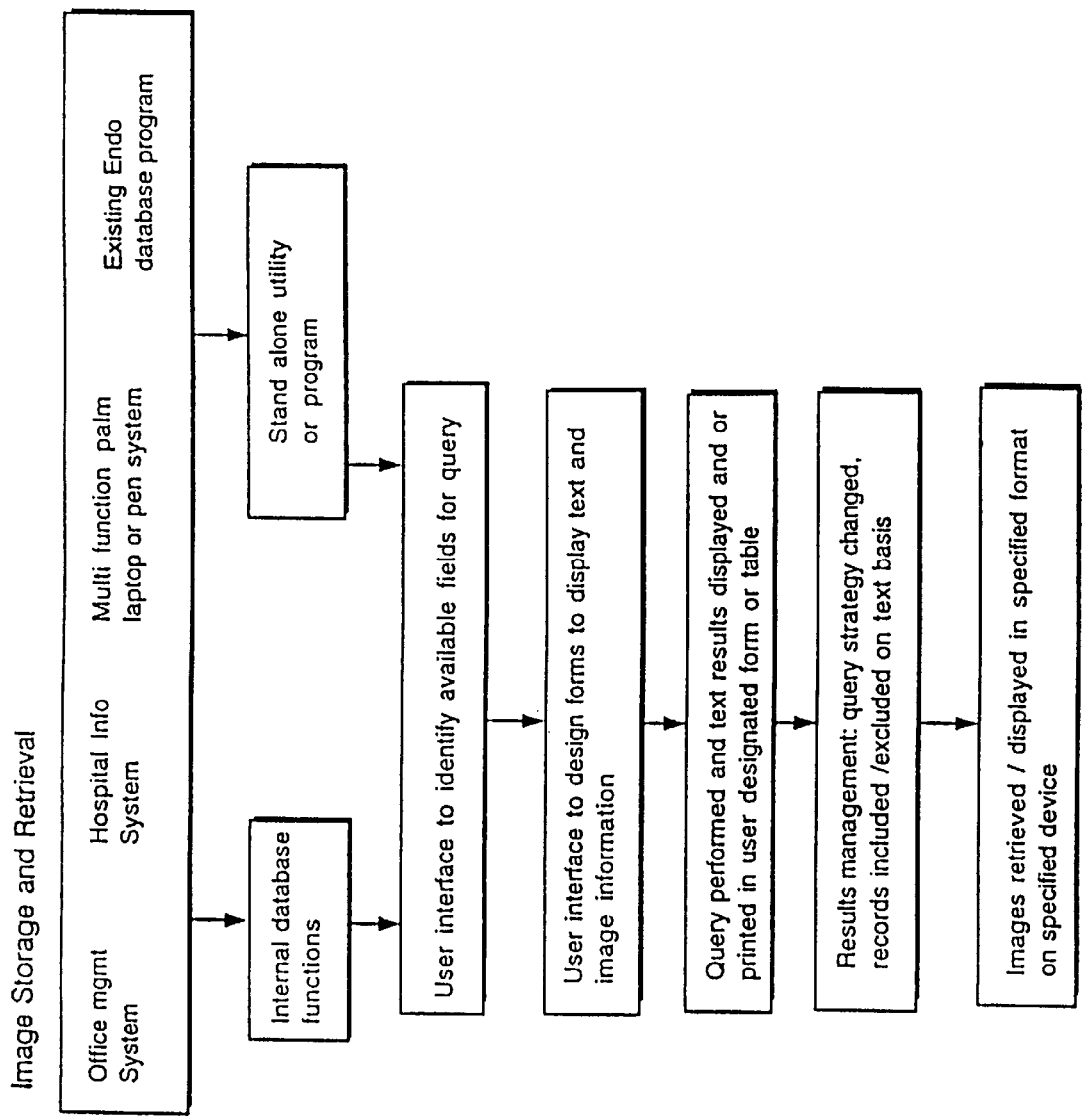

FIGS. 17 and 18 illustrate procedures for storing images in and retrieving images from an image database. The image database can reside in any suitable memory device in system 10 (e.g., disk storage).

Slide Presentation System:

The system automates production of slides by means of a style engine. The style engine takes simple text information to be displayed on the slide, and produces a complex graphical design that is pleasing to the eye, and consistent throughout a presentation. The graphical design includes color, spatial arrangement, bullet marks, justification, and other graphical enhancement instructions. The style engine automatically positions text, graphical elements, and images without additional operator input, other than the user typing in the desired text or selecting the desired image. In one embodiment the styles are tailored to meet the needs of the medical presenter, but the engine is generic, and additional style parameters can be added.

The style engine is also responsible for updating existing presentations. Selection of a style changes the appearance and attributes of slides previously created, or imported. Colors, sizes, positioning, font, and text selections are changed so that all images in the presentation are consistent in look, feel and layout.

Following are some examples of the style engine functionality: The slide construction screen has designated areas for titles, subtitles, body text, bullet text, multi-column text, and images. Not all slide screens contain all elements. The user simply enters text, and the style engine adjusts the font size, position, and color of the slide composition by style engine rules. The style engine determines what information the user has entered, and maximizes use of the available imaging of the slide film. Elements are sized and colored according to a schema for the designated style. Each element is dynamically scaled so that the proportion of title to subtitle to body text or other elements is maintained, and the margins are not violated. The engine automatically compensates for elements without entry by centering, sizing, and scaling the information on the slide. Algorithms are used to determine leading spaces, which are preserved, from trailing space, which is truncated. When proportional fonts are selected, the style engine performs kerning operations to normalize the appearance and spacing of the text. The style engine will determine global limits from text font and size for a given presentation, so that slide to slide variation of font, size color, and positioning will be constrained according to good presentation guidelines. These limits, or guidelines, are stored in text files, so that the operating range of the style engine can be modified at any time.

Clipboard Function:

Images and data can be collected from across many records or storage devices without respect to user or media identity using the clipboard device. A record or device is designated as the recipient for data. Searches of single or multiple databases and devices may be performed without respect to media or database identification. When the desired information is located, the clipboard function copies the selected information or images to the specified recipient media and file.

The clipboard mechanism can be used to collect images and data from across multiple users, multiple media, and multiple storage formats or databases. This function is used to collect a pertinent subset of images, across media, formats and users. For example, a collection of images may be created to provide ready access to images to be used by the slide module in creating a presentation. This mechanism can also be used to import or export data to external database applications or storage devices. For example, a small number of relevant images may be placed onto a PCMCIA storage device for use in a laptop computer or presentation program.

Arithmetic Logic Unit:

The system includes signal processors running at real-time pixel clock speeds that perform signal-to-noise analysis, and apply correction to the signal prior to display.

Slide-Making Function

Figure 13:
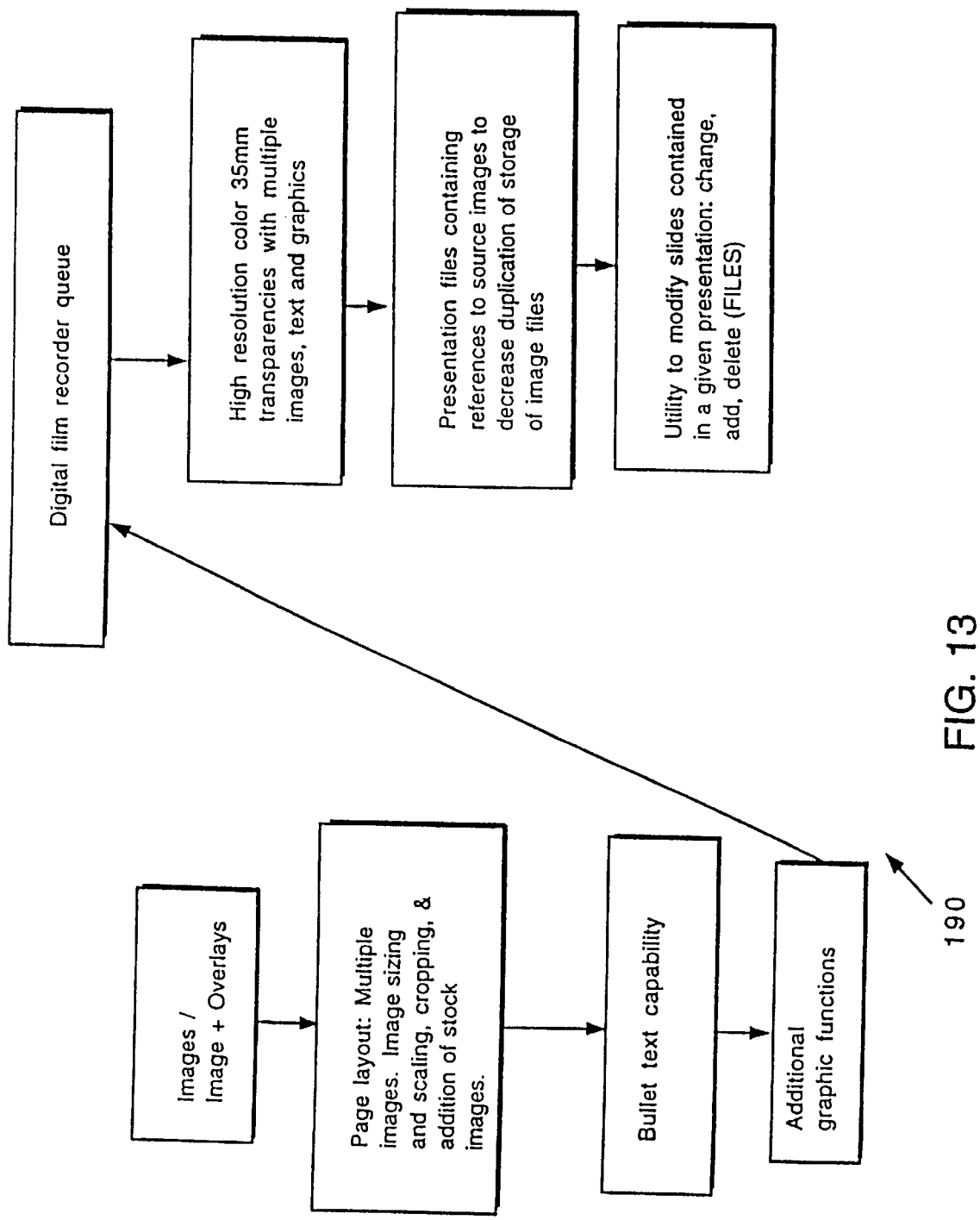
FIG. 13 shows a procedure performed by the system of FIG. 1 for producing slides from the acquired images.

Referring to FIG. 13, system 10 also performs a slide-making function 190. Slide function 190 allows:

1. rapid and easy integration of high quality digitally processed images acquired using the OR image capture system discussed above; and
2. a method for constructing presentations. A presentation consists of a series of slides that contain formatted layouts of image, text and graphic information.

Image information may be used by many presentations, and stored only once. The system database (discussed below) allows for this by supporting "one-to-many" and "many-to-many" data relationships. Slides, images on slides, or any other element comprising a slide may be shared by greater than one presentation. An object will continue to exist until all presentations that call it are modified or deleted.

Slide function 190 performs the following operations:

Image processing functions

This part of the system allows the user the ability to specify parameters normally specified by the preference database, thereby allowing manual control of digital image processing functions in addition to the preference database based processing methods.

Scaling and positioning

Multiple images may be scaled and positioned on a single slide. The appropriate scaling and positioning are done on the fly from the appropriate source image, leaving the source image unchanged.

Text

High quality anti-aliased text is available in multiple fonts and point sized for overlay and text functions.

Preview Mode

Image information is displayed in a "rough cut" or approximate view version for processing speed. A presentation may be viewed as multiple miniature representations of the component slides on a single screen. The slides can be moved or modified using any pointing device to restructure the presentation. This can be done on a laptop, personal computer, pen based system, or workstation.

Batch Print

A presentation may be-queued for printing. The system will automatically control a digital film recording device, transferring the digital files to film. Automatic recording of number of available frame and errors will be incorporated. This should allow for most slides to be printed and discarded, allowing all filing to be conveniently located on the machine.

Preview and Edit

A simple interface allows the operator to view and edit slides in a so-called "what you see is what you get" presentation. During the preview mode, the actual visual is formatted and presented to the user at the full resolution of which the selected display device is capable.

System Software—Overview

The external view of system 10, to the end user, is that of a medical-specific application, designed to handle both the capture and storage of real-time data, as well as the maintenance and manipulation of the data and relationships of the data to other associated information. This external view can be represented by FIG. 19.

Figure 19:
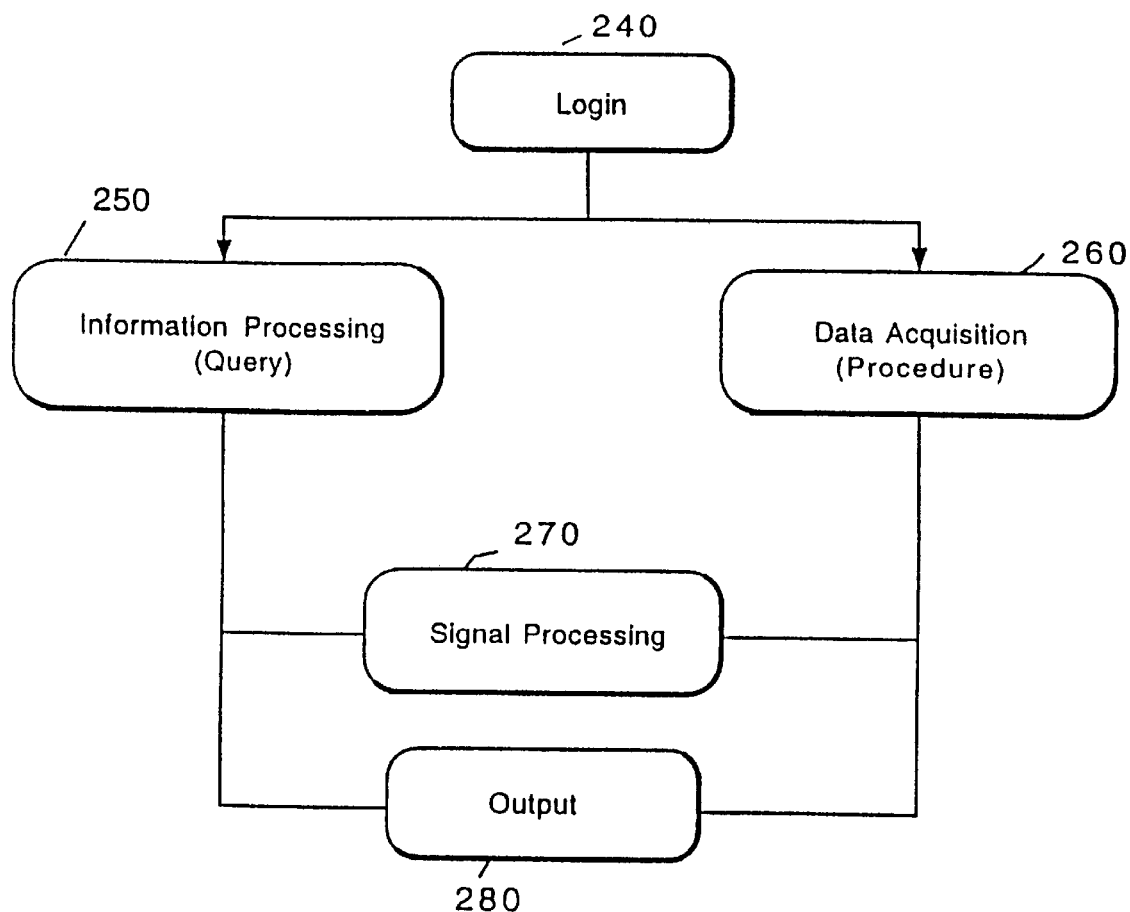
FIG. 19 is a flow chart that shows the operation of the system of FIG. 1 from the standpoint of the user.

As shown by FIG. 19, the end user first encounters a login procedure 240, which admits him or her to system 10. The user may then go to either Data Acquisition (Procedure) 260 or Information Processing (Query) 250. Both of these two sub-systems can invoke a signal processing subsystem 270 and an output subsystem 280.

The primary non-medical features of program 14 (FIG. 1), from the end user's view, include:

1) Simplicity of use

Program 14 has been designed to be as simple as possible to the end user. This means that program 14 uses heuristic approaches, in many cases, to avoid having to ask complex questions to the user.

2) Platform Independence

Program 14 is designed to run on a multitude of platforms, and to allow many forms of input and output. This allows program 14 to be easily maintained, upgraded and expanded, and is not limited to availability of specialized equipment. Program 14 is designed to run on multiple platforms, including DOS, WINDOWS, UNIX, NEXTstep, and workstation architecture.

System Software—Technical Description

Program 14, as illustrated in FIG. 19, embodies a much larger set of engines (i.e., software modules) running under the surface. Each engine is designed to provide a fairly easy mechanism for maintaining a flexible environment. Flexibility includes the ability to make major changes in both the functionality and presentation of the software, as well as to provide platform independence for easy integration of new software and hardware.

Figure 20:
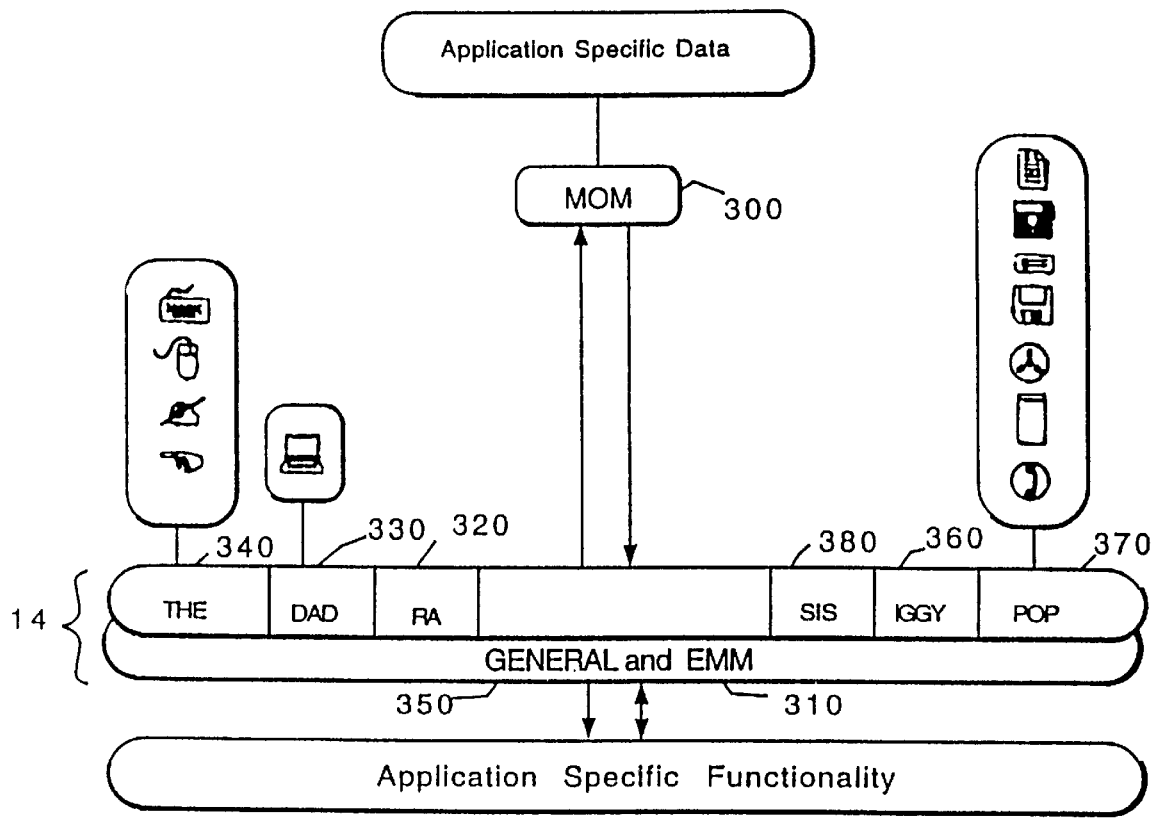
FIG. 20 shows modules of a software program that controls the overall operation of the system of FIG. 1.

Referring also to FIG. 20, program 14 is divided into several engines each of which is devoted to a particular portion of the application, and is designed to integrate well with the other engines in the application. The engines included in this application are described below:

| | |
|---|---|
| MOM 300 | Menu management engine |
| EMM 310 | Memory management engine |
| RA 320 | Raster engine |
| DAD 330 | Platform independent display engine |
| THE 340 | Input device engine |
| GENERAL 350 | general handlers for system independence |
| IGGY 360 | Signal processing engine |
| POP 370 | Output device engine |
| SIS 380 | Database engine |

FIG. 20 shows the interconnectivity of the engines, and their overall location within the application.

The following sections describe in detail each of the engines, its purpose and features:

Menu Manager Engine (MOM) 300

Menu management engine 300 handles the creation and maintenance of the entire software application that executes in system 10. To control MOM 300, the application describes menus as a series of encapsulated data arrays. The data arrays embody the following information:

1) Top Level Menu Array
   A) Menu Location
   B) Menu Size
   C) Menu Background Graphics
      a) RA Graphic token list
   D) Menu Help Data
   E) Menu EMM memory address
   F) Menu efficiency tables
   G) Menu Button Information
      a) Button Count
      b) Button ID
      c) Button Location
      d) Button Size
      e) Button Graphics
         1) RA Graphic Token List
      f) Button Function Pointer
      g) Button Attributes
      h) Button help text With this technique, the entire control path of the application is described in data arrays, instead of embodied in code. This flexibility allows the program control, as well as the look and feel of the program, to be changed by simple manipulation of data, instead of with code. Furthermore, this technique allows the program itself to make critical control path and look/feel changes, on the fly, while the user is running it. This capability allows the users to custom design the program to their tastes, affording an individualized fit to each and every user. The only thing the applications programmer needs to provide is the controlling data arrays (described above) and the functionality (action) for each "button" described in those arrays.

MOM 300 is designed to handle any number of "windows" on a display screen. The above data arrays describe both the look and feel, as well as the functionality of each window. A "window" may consist of a background and one or more buttons. A background describes how the window appears, and is not limited to any particular look. A button is an entity that exists on top of the background, and provides either information or functionality. When providing information, the button retrieves some data and displays it to the user in an understandable manner. When providing functionality, the button causes some action or actions to occur when the user "pushes" the button (e.g., by touching the button on a touchscreen or activating it with a mouse).

MOM 300 uses an integrated help system to allow the user to query both windows as well as buttons to see their functionality or use before being required to actually use the system. As can be seen by the above array, the help system is embodied in the menu and button descriptions themselves, and thus afford easy change and upgrade with the software.

MOM 300 allows the display of windows to overlap, and handles complete maintenance as to the order and depth of windows, as well as the displaying of the windows that become revealed through use.

In addition to the multi-window approach used by the menu manager, MOM 300 also provides multi-processing on the window level, as the user is never restricted to working only on the "top" window. Through dynamic array switching, MOM 300 allows the user to select any visible button, regardless of the associated window or its depth in the screen. Because of this, MOM 300 implements a flat window scheme in which no window has precedence over any other window.

By providing this level of management, the ease of use to users is greatly improved by always allowing the users to "have their way." However, to provide total flexibility, MOM 300 does include an ability to simulate the more traditional hierarchical menu structures, if the need arises.

MOM 300 performs its work in a fairly straightforward manner. When an application begins to run the first thing done by the program is to invoke MOM 300 routines to open one or more windows. Once this is accomplished, the program then invokes MOM 300, which takes complete control of the program from that point on.

MOM 300 analyzes the existing menu structures and begins to query the users requests via THE engine 340.

Display of the menus, as well as display of the user's input device and selection of choices, is handled within MOM 300 by calling RA engine 320 to draw the desired information, and DAD engine 330 to display it to the current output device.

No rules are placed on what can be performed by the functionality invoked by MOM 300 via the data structures. If desired, windows that were opened at the beginning of the program may be closed, and new windows opened. Likewise, any number of additional windows may be opened. These actions may occur in response to users activating various functions on the existing windows. This may even include the restructuring of buttons and data within existing windows. For example, the user may select a button that causes half of the buttons on a current window to be replaced with an image. This type of dynamic remodeling of the menu manager environment is totally handled by MOM 300. The functionality merely expresses the changed data arrays and MOM 300 handles the reintegration of the data into the existing environment in a seamless way.

MOM 300 is also responsible for all event handling at the menu level. MOM 300 can be made to poll events at every input device cycle, and maintains, among other things, a real-time clock for timing of events and maintenance of a time-of-day clock. MOM 300 uses THE engine 340 for event polling, but allows button functionality to uncouple event polling for specialized event handling within a button's action.

MOM 300 never terminates, unless all windows are closed without a new window being opened prior to functionality return. Besides this method, the only other method of termination is direct exit within a function.

Memory Management Engine (EMM) 310

EMM engine 310 is responsible for the allocation, maintenance and freeing of the data arrays used by RA engine 320 and the other functionality portions of the program. Despite the fact that modern programming software provides memory allocation, the use of EMM engine 310 assures platform independence when moving between software platforms as well as hardware memory platforms.

EMM engine 310 is a fairly simple code system that allocates memory in "pages" or "blocks" when requested by the rest of the software. EMM 310 maintains data lists to track the memory, and provides boundary checking as well as freeing of the data when its use is complete.

Finally, EMM 310 also provides the ability to query the memory system for remaining quantity and availability, allow the software to provide status, as well as predict remaining capability.

EMM 310 is used by MOM engine 300 to allocate the memory used for the windows (see the section below on RA engine 320 for a more detailed description) as well as being available to all the other engines as needed.

Raster Engine (RA) 320

RA engine 320 is the main drawing engine responsible for drawing the menus and their associated buttons and backgrounds. Because this software system is designed to be platform independent, RA 320 does not draw to any output device. Instead, RA 320 interfaces with EMM engine 310 and draws to EMM allocated memory. Actual display of the windows on the users display device is handled by DAD engine 330. This type of architecture is termed a virtual frame buffer.

RA 320 is driven directly by MOM 300, and in some cases by the application functionality itself. RA 320 is a table dispatched service and takes as input a pointer to a heterogeneous data array. This data array consists of pointers and data, where the pointers correspond to a token list that embodies a primitive graphics language.

The token list described by RA 320 contains the minimum needed set of drawing devices to render all menu drawing. This includes gradient rectangles, anti-aliased and non-antialiased text, circles and lines, as well as more complex concepts such as buttons, sliders, controls, LED's, and textured backgrounds. In order to provide capabilities that may be needed later in the development cycle, RA 320 also provides programmer definable tokens, via a functional token, with which programmers can vector to their own code during a RA token execution. This enables the program to draw any type of object, even objects never conceived before in the software.

RA 320 is limited to drawing to a single window at a time, and may not mix drawing to different windows within a single token download. Therefore, it is up to MOM 300 to direct RA 320 as to the appropriate window for drawing, as well as providing RA 320 with the correct token list, as extracted from the menu arrays.

Because of the self-modifying nature of the software, as well as its platform independence, RA 320 is designed to allow self-modification during the execution of an RA token list. In other words, a token list can self-modify while executing, allowing decisions to be made on the fly, as to future drawing that is still down-stream from the current point of token execution.

RA 320 always draws via EMM engine 310, in a standard method. While the method is modifiable, it is a fixed in code by the programmer. For example, within this application, RA 320 is defined to be 24 bit (8 bit per pixel) in a Packed architecture (RGBRGBRGB . . . ). By splitting RA 320 and DAD 330 apart, and allowing DAD 330 to handle device particulars, DAD 330 can color reduce/expand, as well as resolution reduce/expand the RA maintained EMM memory buffers when displaying to any device.

Font drawing is handled in RA 320 by use of precomputed raster font tables. The font tables contain one byte per pixel, which indicates the natural antialiasing of the font at that pixel. Fonts are encoded so as to be both proportional as well as non-proportional, and any font may be displayed in any combination of antialiasing and proportionality. When fonts are displayed, an additional font transparency sets the level of opacity, allowing for drop shadows and other effects. Font color is specified as a 24 bit (RGB) value, which is used with the transparency and antialiasing information to calculate the appropriate color for each pixel. The software allows any number of fonts to be loaded concurrently, and fonts may be switched dynamically, on a character by character basis if desired. Font concurrence is only limited by available memory (as all fonts used are always resident).

Platform Independent Display Engine (DAD) 330

DAD engine 330 handles actual updates of information to the user's end display device. Since the software system is device independent, DAD 330 coordinates requests from MOM 300 and the user's functionality, and reads EMM memory and displays the contents of EMM memory to the current device.

Basically the cycle works as follows: MOM 300, following advice from the menu structures, instructs RA 320 WIto draw the various windows to EMM memory. After RA 320 completes the drawing, MOM 300 then instructs DAD 330 to take the completed EMM memory and display it on the current display device.

When DAD 330 receives an instruction to display a piece of EMM memory, it consults the MOM data structures to determine the location of the memory, and the desired location of its display. Because DAD 330 is purely BLIT oriented (e.g., high speed rectangles), the drawing is both efficient and space saving. Because all display devices have inherent differences, it is DAD's responsibility to call the appropriate routines at the proper time, for each display device.

When a new device is added to the system, only a small handful of routines need to be supported for the device. Of the total roster of routines, only routines which the display device is capable if need be supported. Routines that are not possible for that display device need not be stubbed, and DAD 330 is simply informed of their absence and handles it gracefully. The routines required embody a small set of primitives, which include area blitzing, line blitzing, high speed rectangle drawing, high speed or outlined rectangle drawing and cursor support. Other routines, not necessarily supported by all devices include, acquisition, high-speed unpacked blitting and automatic packing and unpacking routines.

Because the amount of code for support of a driver is relatively small, the drivers are compiled directly into the software. This capability allows DAD 330 to actually maintain and provide output to multiple devices simultaneously, making it attractive for multiple displays as well as switching between hardware on the fly.

In order to make DAD 330 handle the platform independent drivers, the software calls a standardized set of routines, which are table dispatched at runtime. Because of the table dispatch method, no comparisons are required to locate a routine within a driver. Instead, all execution is handled by hashed indexing that provides near-instantaneous access to all drivers an all functions. Note that because DAD 330 is responsible for both input and output display devices, it handles any video acquisition required by video data software within the user's procedure program. This requires that DAD 330 coordinate with SIS 380 and MOM 300 at the proper time, for control and decoding of incoming video.

Input Device Engine (THE) 340

THE engine 340 is designed to be a device-independent input event handler. THE 340 is invoked by both MOM 300 and the user's functionality, to retrieve spatial and textual information from the user. Because the software is input device independent, THE 340 is responsible for the combination of multiple pointing devices 58, and can handle more than one input device simultaneously, as well as being able to switch input device context on the fly.

THE engine 340 is basically divided into two sections: textual and spatial. The textual handler involves reading textual data from keyboard devices and transmitting them, when requested, to MOM 300 and functional software. Textual handling includes not only input and maintenance of text buffers, but also flushing of all textual queues.

Spatial handling is performed by determining the location and types of input devices. Because input devices fall into two categories, absolute and relative, THE engine 340 automatically converts all coordinate, regardless of their type, into absolute coordinates. These coordinates are automatically clipped, by THE engine 340, against the current screen resolution as defined by DAD engine 330.

One aspect of THE engine 340 is its coupling with MOM 300 for mouseless handling of menu structures. Because MOM 300 allows menus and buttons to exist anywhere on the screen, even layered, the software that allows the user to move from "field" to "field" (including buttons) must be able to dynamically analyze the "best next" button to go to, from the current button. This is especially important when considering the fact that the user may modify the look for the menus, on the fly. While the program allows for a fixed transition from button to button, a dynamic method of determining the most logical "next choice" for the user is implemented as follows. THE engine 340 handles this, with help from MOM 300, by keeping track of two cursor locations: the current absolute cursor location, and the current field cursor location. The field cursor marks the current (or most recent) choice executed by the user (e.g., the last button picked). When a cursor movement command is detected by THE 340, it uses MOM engine 300 to retrieve the menu descriptions, and analyzes these descriptions in an attempt to determine the best location to move to, and then performs the move to that location. This form of dynamic sensing affords the most flexibility to the entire application.

General Handlers for System Independence (GENERAL) 350

GENERAL engine 350 handles all routines that are fairly standard, but that for one reason or another are desirable to have under platform independent control of the application. This includes items such as non-EMM engine memory acquisition and freezing, as well as file I/O. GENERAL engine 350 is present to give a simple and global mechanism for error control and handling. This provides the software package with a uniform mechanism for error recovery, which otherwise may be handled in a less than elegant way by the operating system of run-time program.

Signal Processing Engine (IGGY) 360

IGGY engine 360 is responsible for all digital signal processing of acquired wave-form (i.e., image) data. IGGY 360 is commanded primarily by MOM 300 and the functionality used to perform some form of wave-form processing (usually image processing). Instead of being an integrated engine (as are MOM 300, RA 320, DAD 330, and the other engines), IGGY 360 is a set of separate routines, which may be used and combined to perform high level processing of acquired data.

Due to the nature of the application, in that the end user does not possess the education necessary to perform high-end signal processing, IGGY 360 is designed to have heuristic processes that allow it to analyze wave-form data and determine the best enhancements necessary. IGGY 360 can use MOM 300 to request minimal information from the user, but in general does not do so except in the simplest of cases.

IGGY 360 embodies at least the following basic signal processing techniques:

1. Histogram Analysis
2. Histogram Stretching
3. Histogram Equalization
4. Noise Analysis
5. Noise Reduction
6. Area of Interest Location
7. Unwanted Area Removal—i.e., rather than compress the data, only meaningful data (such as the picture of the surgical site) is retained, while other data (such as borders that contain no real picture information) are discarded.
8. Sharpening
9. Blurring
10. Feature Extraction
11. Feature Highlighting
12. Blending
13. Artifact Removal
14. Non-linear balancing
15. Colorization.

Though IGGY 360 provides these services in an on-call manner, the analysis services utilize heuristic techniques to determine whether the other services are required to provide the best output data possible.

Output Device Engine (POP) 370

POP engine 370 is to the output devices as DAD 330 is to the input devices. For each output device supported, POP 370 provides interface mechanism for that device. POP 370 also provides limited input from some of these devices, as the device requires. POP 370 is responsible for maintaining output (and sometimes input) to the following devices:

1. Printers (color and black and white)
2. Film Recorders
3. Data Recorders
4. Tape Drives
5. Disk Drives (hard and floppy)
6. FLASH cards (PCMCIA)
7. Networks
8. Modems It can be seen from the above list that POP 370 is responsible for some diverse device handling. POP 370 places the devices into "like" categories, and provides a uniform mechanism for calling "like" devices. For example, all drives, flash cards and networks are driven in a like manner, while modems have their own mechanism, as do printers and film recorders. Since MOM 300 directs the output activities, POP 370 is never confused as to how the service is intended (e.g., each service is specialized, and thus POP knows the appropriate need and duty).

While most of handling provided by POP 370 requires simple interfacing to outside drivers, or the operating system, the printer and film recorder interfaces of POP 370 are highly particular to the device being addressed. Furthermore, because of all the possible formats for output devices, POP 370 interfaces with MOM 300 to provide the user with a visual mechanism for the specification of output format. For example, under printer interface, POP 370 can direct MOM 300 to display a grid of images, and have the user select the appropriate image and its location. Furthermore, POP 370 interfaces with RA 320 to allow the user to annotate the images prior to output. POP 370 handles interpolation of incorrectly sized data, and can utilize in-memory fonts as well as printer provided fonts, depending on the hardware capabilities.

Database Engine (SIS) 380

SIS engine 380 is the database handler. It is responsible for handling all database activities that include user management, forms management, data management and signal processing management.

User management is invoked by MOM 300 to confirm a user and to set a users profile for the display of MOM menus. Forms management handles the design, storage and retrieval of forms. Data management handles the storage and query of data from within forms. Signal processing management is a subset of data management, and is responsible for the handling of signal data within a form.

Overview of Flow Control

As discussed above, program 14 is designed to be a specific medical application, even though the engines provide a much greater, and universal capability.

The overriding flow control is a section of the software that dictates to MOM 300, POP 370, SIS 380, and IGGY 360 a particular method to follow for user flow control. It is this overriding flow control that provides much of the automatic handling that is required by the naive user.

Referring also to FIG. 19, when the user invokes program 14 at login time, the user is greeted by an opening screen and requested to enter a user name and password. Once entered, these elements are cross compared, via SIS 380, against the valid users in the database. When a valid user is identified, his user profile is loaded, and MOM 300 is informed of any changes to the environment.

If the user has an associated procedure form with his or her login, the user is asked whether this is a procedure. If the answer is affirmative, procedure flow control 260 is followed; otherwise, information flow control 250 is followed.

Procedure Flow Control 260

Once procedure flow control 260 is accessed, the procedure handler accesses the user's procedure form and displays it to the user. This is some form, entered for or by the user, when the user is given original access to the software. The form that is assigned to the user may be modified at any time via the information processor.

Once the user fills out the form, the procedure flow control 260 is launched. This causes DAD 330 to invoke acquisition and control is switched to the user. THE engine 340 monitors a special remote control, used during procedures (or, optionally, the keyboard), and causes various video functions to be executed. These include, but are not limited to:

1. Zoom IN and OUT of the live video image
2. Freezing the live video signal, and then discarding it
3. Freezing the live video signal, and then saving it sequentially via POP 370
4. Reviewing all currently acquired video signals
5. Executing a TOUR (directed capture sequence)
6. Adjustment of the input video parameters Captured images are sequentially numbered and named, and are stored on the current mass storage device via POP 370. At the end of the procedure, SIS 380 is automatically called to store all, or only approved images into the database, associated with the current form.

During the REVIEW process (122, FIG. 6), the user may review all captured images, and optionally delete unwanted images or invoke special image processing on selected images. Images selected for special image processing are processed automatically and overwritten with the new results. When images are overwritten with the new results, an undo file is created, which allows the user to restore the original image file.

Upon exiting procedure 260, the user is given the ability to download the acquired data to a removable media device (e.g., FLASH memory, etc.), and then is logged off the program.

Information Processing Control 250

Information handler 250 is invoked upon successful login, when the user either does not have an associated procedure, or does not wish to access procedure. Once in the information processing system, the user is first greeted with a list of available forms (via SIS 380). The user may select an existing form, or select a "new form" option to create a new form. If the user opts to create a new form, the various form elements that are available are shown to the user, plus the ability to create new form elements. A form element is any item when exists on any other form.

When the user picks an existing form, the form is loaded with blank data. The user may fill out one or more of the fields in the form, and either enter the form into the database (e.g., enter the instance of the new data) or else request a query. When a query is requested, SIS 380 will attempt to fulfill the missing elements of the form, based on the fields that have been filled in. Upon retrieving the list of available responses, the user is shown the list and allowed to pick an item from the list. Once picked, SIS 380 will load the form with the appropriate data, and will display it to the user. Images, or other signal processing data within the form, when selected, will invoke a image browsing menu that displays all associated images with the form. Further selection of an image will cause IGGY engine 360 to be accessed for full signal processing by the user.

Information processing procedure 250 also allows the user to format and output query responses to the printer, in a variety of looks, all handled by POP 370.

Finally, for system administrative users, information processing procedure 250 allows new users to be added to the system, and existing users to be removed from the system.

Database Configuration

Figure 21:
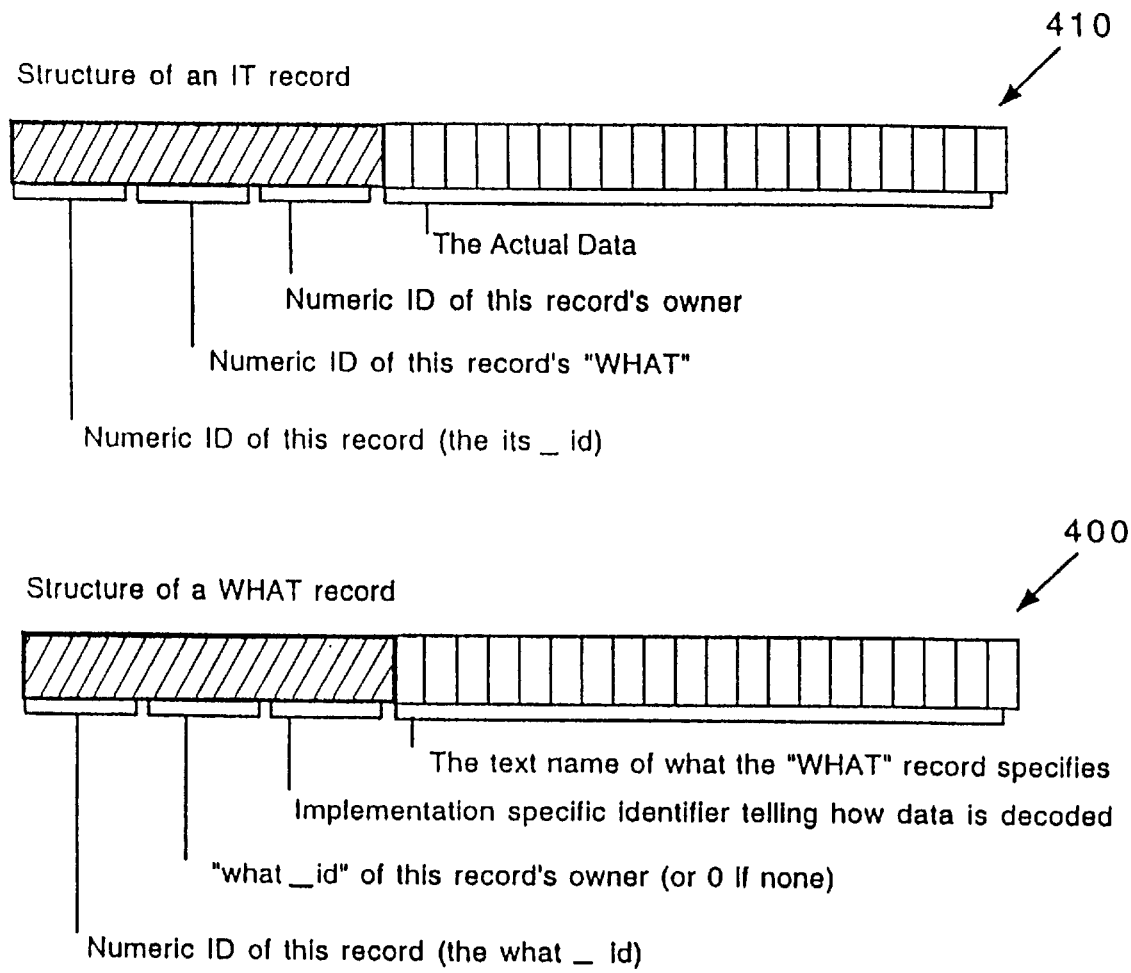
FIG. 21 is useful in understanding the structure and organization of the databases used in the system of FIG. 1.

Referring to FIG. 21, preference database 20 and all image databases are organized in a manner that maximizes the flexibility of adding, modifying, or deleting information from the databases at will, without rebuilding or restricting availability of data. The structure of the databases is relatively simple, which keeps the data model independent of features of host data storage. In addition, database subsets (datasets) can be derived, extracted and manipulated remotely and then merged back.

Each data element is stored independently in database storage. That is, there is no record relative pointer structure in the dataset. All "pointers" are data relative. One advantage of this arrangement is that if a database file is damaged, pointer chain corruption (which could damage other stored data) is avoided.

A dataset may be transformed into plain text to allow for portability.

Two methods are used to store data:

System oriented data such as user accounts and associated settings, attached device configurations (printers and video), and other such information is stored in standard "flat" files.

Patient data records are stored in a relational database designed specifically for the present system. The database is designed to meet the following criteria:

1) host machine independent;
2) unlimited data types;
3) ability to add/delete data types during run time;
4) variable-length, co-existing records;
5) speed of access regardless of the number of records;
6) ability to extract a sub-database, modify that sub-set, and merge the data back into the host database while retaining complete relational integrity;
7) no data space is used for fields that contain no data;
8) all data (including numeric data) is stored as character strings allowing quick, consistent query operations.

"What/Its" design elements:

The database consist of just two record types:

1) the "What" records that hold the definitions describing the kinds of data in the dataset;
2) the "Its" records that contain the actual data along with information on the type of data and the owner of that data (another "Its" record).

Implementation:

"What/Its" is implemented as a "layer" on top of an existing database. This allows for maximum flexibility and portability to future computing platforms. In one implementation, the commercial database product "Raima" is the host database.

Here is the "What/Its" schema as implemented in "Raima":

```
/***********************************************/
database What/Its {
    data file "dimsum.dat" contains what,its;
    key file "dimsum.key" contains what_id,what_owner,
            its_id,its_owner,its_what,its_tag;
    key file "dimsum.kit" contains its_data;
    record what {                    /*field types*/
        unique key long what_id;     /*field key*/
        key long what_owner;         /*key of its owner*/
        char what_name[32];          /*field name*/
        long what_look;              /*it's appearance*/
        int what_unique;             /*it's a unique field*/
    }
    record its {                     /*data item*/
        unique key long its_id;      /*its key id*/
        key long its_owner;          /*key id of its owner*/
        key long its_what;           /*what kind of data is it?*/
        key long its_tag;            /*query flag*/
        key char its_data[64];       /*the data itself*/
    }
}
/***********************************************/
```

Record the Field Descriptions:

"what" records

These hold the field "what" definitions describing the kinds of data in the dataset.

"what_id" field is a (long) generated when a new "what" is instanced. It will always be a number that is unique to the dataset. "what_id" is used as the internal key within a dataset used to specify what an "it" record's "data" field record contains (i.e. "Last Name," "Patient Address").

"What_look" field contains a (long) whose value is used internally by dimsum to define how the data field is interpreted (i.e., string,integer,date,imagefile).

"what_name" field contains the ascii text name of a field type. It is used when choosing a field when defining a form. This field is filled when a new field type is created at form definition.

"its" record

These records contain the actual dataset along with information on the "what" of the data and it's owner (as a pointer to another "it" record).

"its_key" field contains a (long) that is unique among "its_key" fields within the dataset. It is the true and ultimate identifier of the data item in a dataset.

References to "its_key" occur in two other fields in an "it" record.

1. If the "its_owner" field is non-0, it will be a "its_key" to the data's owner "it" record.
2. If "its_type" is 0 (specifying a reference record), the "its_data" field will contain a "its-key" in ascii format. This allows one-to-many relations within the dataset.

"its-owner" field contains a (long) "its_key" that points to the data's owner "it" record.

"its-what" field contains a (long) "what_id" that specifies the nature of what is contained in the "its_data" field.

"its_data" field is an ascii string that holds the data. "Its-data" might optionally contain an ascii representation of a "its-key" defining a reference "it" record.

In the specific implementation described above, data is limited to a maximum of 32 bytes for one specific data element. Any length may be used.

Images and free-form text files are used in operation of the invention. Instead of storing the image and text data in the database, only the file name containing the data is stored in "What/Its."

ANSI "C" code example:

This is an example routine showing how the "What/Its" database is used. The example given here shows how a record might be added to the database.

```
/**********************************************************/
    Routine:      SIS_enter
    Description: Add a What/Its record to the database
    Syntax:       r=SIS_enter(strings,whats,count);
                  char *strings = list of fields w/queries
                  long whats[] = list of what strings are
                  int count = # of string/whats pairs
    int r = 2 if no key existed to allow enter of a new record
        r = 1 if record already existed and no enter took place
        r = 0 if record enter was successful
/**********************************************************/
int SIS_enter(char *strings[],long whats[],int count)
{
int nokey,i,j,k,deepest;
long keywhat;
char key[65];
   nokey=1;
   for(i=0;i<count;i++) {
      if(SIS_what_is_unique(whats[i])) {
         strcpy(key,strings[i]);
         keywhat = whats[i];
         nokey=0;
         break;
      }
   }
   if(nokey)return(2); /*no key . . . can't create! */
   if(d_keyfinds(ITS_DATA,key,SIS_DB) == SIS_NOTFOUND) {
      goto notakey;
   } else {
      nokey = 1;
      while(1) {
         d_recread( (char*)&its,SIS_DB);   /*get existing */
         if(its.its_what == keywhat) {
            nokey = 0
               break;
         }
         if(d_keynext(ITS_WHAT,SIS_DB) == SIS_NOTFOUND) break;
      }
      if(!nokey) return(1);
   }
notakey:
      for(i=0;i<MAXQ;i++){
         taglist[i] = 0;
         ownerlist[i] = 0;
      }
      deepset = 0;
         for(i=0;<count;i++) {         /*clear buffers*/
            taglist[i] = SIS_what_depth(whats[i]; /*get it's
                                                    depth*/
            if(deepest<taglist[i]deepest=taglist[i];
                              /*remember deepest*/
         }
         for(i=0;i<=deepest;i++) {      /*thru the depths*/
            for(j=0;j<count;j++){       /*do all that are
                                          this deep*/
               if(taglist[j]==i){ /*this is one at our level*/
                  if(!SIS_what_is_unique(whats[j])) { /*HERE*/
                     its.its_id    =0;              /*its_id*/
                     its.its_owner = ownerlist[j]; /*its_owner*/
                     its.its-what  = whats[j];      /*its_what*/
                     strcpy(its.its_data,strings[j]); /*its_data*/
                     SIS_create_its();              /*store to db*/
                  } else {
         if(d keyf ind(ITS_DATA,strings[j],SIS_DB)==SIS_NOTFOUND) {
                     its.its_id =0;                 /*its_id*/
                     its.its_owner = ownerlist[j];  /*its_owner*/
                     its.its_what = whats[j];       /*its_what*/
                     strcpy(its.its_data,strings[j]); /*its_data*/
                     SIS_create_its();              /*store to db*/
                  } else {
                     d_recread( (char*)&its,SIS_DB);/*get existing*/
                  }
                  for(k=0;k<count;k++){     /*set the owner list*/
                     d_keyfind(WHAT_ID,&whats[k],SIS_DB;/*get each
```

```
                            what*/
        d_recread((char*)&what,SIS_DB     /*if this
                            owner*/
        if(whats[j]==what.what_owner)
        ownerlist[k]=its.its_id;
      }
    }
  }
}
TOP_show("New record created.",OK_COLOR);
return(0);
}
/*************************************************/
```

Record Structure

Dataset storage is implemented using two record types, the "what" record 400 and the "it" record 410. "What" records 400 describe the data dictionary, while "it" records 410 contain the actual data.

Consider the following sample schema definition (in this case, using the RAIMA database):

```
record what {                   /*field types*/
    unique key long what_id;    /*field key*/
    key  long what_owner;       /*key of its owner*/
    char what_name[32];         /*field name*/
    long what_look;             /*it's appearance*/
}
record it {                     /*data item*/
    unique key long its_id;     /*its key id*/
    key long its_owner;         /*key id of its owner*/
    key long its_what;          /*what kind of data is it?*/
    key char its_data[64];      /*the data itself*/
}
```

Each "what" record 400 and "it" record 410 has a randomly generated numeric key that has no special significance other than that it is unique to that specific record in the database.

The data dictionary (i.e., the mechanism that describes the types of data contained in the dataset) is held in "what" records 400. For example, a simple address book data set could require just two "what" records 400—one for a name and one for an address. The actual address book data is held in "it" records 410. One "it" record 410 is used for each name, and one "it" record 410 stores each address.

If the dataset needs to be expanded to include, for example, the telephone number of each address entry, a new "what" record 400 is created for the telephone number. Then, any new entries in the database can also include an associated telephone number—but note that the existing data is not impacted at all. Consider the following example layout of such an address book database:

The "what" records 400 are:

A. 1024:0:name:1
   1024 is the random key; 0 is owner (none); "name" is the text name of the field; 1 denotes alpha string.

B. 3046:1024:address:1
   3046 is the key; 1024 denotes that address is associated with "name"; "address" is the text name of the field; 1 again denotes an alpha string.

C. 4096:1024:telephone number:2
   4096 is the key; 1024 indicates that telephone is also associated with "name"; "telephone number" is the text name of the field; 2 denotes this is telephone number field.

The address book entry "it" records 410 are:

1234:0:1024:John Doe

5748:1234:3046:911 Main St.

8674:1234:4096:(312) 555-1212

In the first it record 410, 1234 is the random key of the record, 0 shows this record has no associated "owner," 1024 indicates that this is a "name" record, and "John Doe" is the name data.

In the second it record 410, 5748 is the random key, 1234 associates this record with the first (John Doe) it record 410, 3046 indicates that this is an address record, and "911 Main St." is the address data.

Finally, in the third it record 410, 8674 is the random key, 1234 associates this record with "John Doe,"4096 denotes that this is a telephone number, and "(312) 555-1212" is the phone number data.

The what/it structure allows several query methods. To find every data item associated with "John Doe" we search the "it" records data fields for "John Doe," read it's key field (1234), and then find all of the records that have 1234 in the owner field.

To obtain a list of phone numbers, we simply scan the "it" records looking for "4096" in the "its_what" field. If we need the name associated with these phone numbers, we look at the "its_owner" field (in John Doe's case it would be 1234) then locate records with 1234 in the "its_id" field —and—1024 in the "its_what" field.

The what/it structure allows several types of data relationships to exist including one-to-one, one-to-many, many-to-one and many-to-many associations. All of these can be created dynamically simply by defining the appropriate "what" records.

Also note that no storage is taken for non-existent data. In the address book example, if there is no telephone number for a given entry, then no "it" record is allocated.

The what/it method also lets us extract a subset of records by first obtaining all of the "what" records and then obtaining all of the desired "it" records by the "its_what" fields.

Preference System:

The preference system integrates system-available resources with user-specified preferences, specialty-specific preferences, or procedure-specific preferences. Entry onto the data entry forms, or logging on as a user results in configuration of the operating environment. Information such as sex, age, left or right side are used by the system so that the operator is not presented with options that would be excluded given other choices already known to the system. The preference database does more than control only the image capture routines. It sends commands to any connected devices that cause them to behave in a specified manner. The Controls are implemented at 3 levels that are hierarchical so that the most specific preference specification will be a procedure-related specification, which builds on a specialty-specific or user-specific preference, all of which are subject to system availability of resources.

The system determines the total operating range for a user. I.e., a user can only use what's there. The system overrides user preferences with a substitution if the user selects an unavailable option. The system sets the available range of operation for each device. I.e., it determines what choices are there for the given device.

Setup of the system occurs on two levels: 1) setup of the system, and 2) setup of a user (typically registered on the removable media).

Setup of the System:

When a system that has not been previously configured is turned on, the system looks for devices that can identify themselves to the software program. Some devices (e.g., video subsystem 34j) can be identified by the software program. Other devices (e.g., an external video camera) may not report to the software program. The interface provides a list of possible connected devices (printers, cameras, storage devices), specification of the identity of the installation (site name) and access to set the system date and time clock. Options regarding operation of devices can be selected at two levels. For devices such as video cameras that have generic classes (e.g., RGB input, Y/C input), option selection is done by selection of the class of devices given in the first option. For devices that have specific control options, selection of the device brings up a second menu of user choices that are preset to the system specified defaults. Once selected, these options form the basis for the connected devices. This may result in changes in the commands that initialize the system. Changes made in the setup will remain in force until the commands are overridden by a user preference, or the setup procedure is repeated. Date and time functions are used to set the system clock and will be maintained by the system clock. Internal accounting is performed for both daylight savings time and a perpetual calendar. The site information is transferred to individual use sessions of this instance of the invention where the individual data form calls for recording of site information. While this setup information can reside on any storage device, in one embodiment, this information is stored on the system storage drive, which is normally not accessible to user accounts.

Setup of a user:

Setup of a user presents a form that contains fields for entry of user login identity, primary and secondary password, user-specific identification, specialty, storage device and other preferences. The login identity, primary, secondary passwords, specialty and storage device selections are required entry. The login id and passwords are stored to the specified user account. In one embodiment, this information is stored on the removable media. The specialty selection copies data entry forms and preferences, and an empty data structure from the system accessible files to a user accessible file. Further user preferences or modifications are copied to the user's account. The information copied occupies only a small amount of storage space on the user's media so that this division of storage is practical. This division of storage allows a single user to use many instances of the machine. Because user-specific information is stored on the removable media, system maintenance and system storage requirements are controlled, and reliability is enhanced.

In the event that operation preferences stored in the user account result in requests of the system that may not be physically possible, the system contains a substitution table that allows the system to substitute the most reasonable alternative to the user choice given available system resources. If no suitable substitute is available, the requested option is simply not allowed. However, all data is stored in such a manner that even if access to a feature is denied, when the same user signs on to a system that has the necessary resources, the system will utilize them as specified by the user preference.

Forms are the final place where preference is implemented, and system and user data integrated. Forms serve both as tools to obtain user keyboard input of data, and director of operations for the system. Selection of specialty loads the specialty specific forms for procedures commonly performed by the selected specialty, and containing data fields for the information commonly associated with the procedure(s) that will be documented using the form. The form also contains the specification for the tour scripts that will be used during the procedure. The forms also contain selections for right, left, male and female that may alter the tours, or prints of the images, and available selections such that only choices related to the correct side and site will be available until a new form is selected or the side, sex or site information is changed (e.g., on a hysterectomy, all prints will show only female anatomy, and male will not be an appropriate choice, whereas on a hernia, male or female will be both necessary and relevant). System and user information including date, time, user id, name and site are automatically entered into the form. Sequence of operations, and availability of system options, and how they are presented to the user can also be specified by the forms. The forms also contain instructions for how the cursor will traverse the form (i.e., where the cursor will move after a given keypress).

Video preferences, remote control operation specification, or other parameters may be attached to a given form. As such, the form is the final entry point prior to starting a procedure. Completion of the form is required before procedures can be initiated.

Setup of forms:

In general, setup of a user will result in access to all forms normally required by the general user. The system contains a capability to modify or design forms. The form builder is considered an advanced feature, and can only be selected by users with appropriate permissions. The form builder consists of a set of tools to specify the appearance of the form, and a visual means to specify the actions of the form. The user can specify data fields, length, content and attribute of fields (text, alpha, numeric, validation range), and can specify what field the cursor should go to next, whether a field is required or optional, and relationship, if any, to other fields in the form (i.e., right excludes left, male excludes female etc.), and the position of the field on the form. The user can also specify a new tour or series of tours associated with the form. This is done by sequential use of the tour creating function. Each sequential image prompt is designated. The filing of the tour images is handled by the system automatically.

The forms can also call on output layout files, such that a form will specify how images captures while using the form will be formatted by the system. In general, these formats are stored on the system storage devices, and used by the forms. The output layouts are constructed such that the form builder can substitute information from the form into existing layouts referenced by a new form. Alternatively, new output layouts can be created and added to system storage to support the form. If this is done, the layout will be attached to the user account, since it will not be available in the general release.

The ability to modify forms is dependent on the What/its data structure. In a typical relational database structure, changes in forms would require an update of the database schema. Records created using the old schema may not be accessible to the new schema and visa versa. With the what/its structure, modifications of the form and additions or deletions of fields are tolerated without compatibility problems. Forms themselves are stored as data files that contain pointers to the appropriate long array that are used to construct them. Data is stored in a schema independent layer as data itself. The database schema, and key management is independent of the data. In one embodiment, Raima data manager is selected for the underlying key management scheme, and hard database schema because of its speed in retrieving data stored with multidirectional pointers that the what/its structure implies.

The presence of tours, and associated printing formats necessitates a method for managing selection of the correct form when a query is performed. For example, a general surgeon has forms for laparoscopic hysterectomy, cholecystectomy and a generic form. A query for patient name John Smith yields a list of matches that have images and data related to specific forms. The system stores a hidden mark that associates a given patient's data with the correct form type. On selection of a given record, the system fetches and displays the data to the user on the proper form, even if it is different than the form used to initiate the query.

Other embodiments of the invention are within the scope of the following claims. For example, while system 10 has been described with reference to endoscopy, the system may also be used for other medical procedures, surgical or otherwise.

I claim:

1. A method of reducing interlaced noise on an interlaced video display device by reducing motion artifacts due to motion that occurs between acquisition of fields of video that comprise a video frame, comprising the steps of:

a) comparing at least one pixel in at least one line of a first field of video with at least one pixel in at least one line of a second field of video that is interlaced with said first field on said video display device, said at least one line of said first field being in close proximity to said at least one line of said second field, said at least one pixel in said first field being in close proximity to said at least one pixel in said second field, b) determining whether a difference between a value of said at least one pixel in said at least one line of said first field and a value of said at least one pixel in said at least one line of said second field exceeds a fixed value, c) if said difference between said values of said pixels exceeds said fixed value, replacing said value of said at least one pixel in said at least one line of said second field with a value closer to said value of said at least one pixel in said at least one line of said first field, d) if said difference between said values of said pixels is less than said fixed value, maintaining said value of said at least one pixel in said at least one line of said second field, e) performing steps a) through d) above for additional pixels in said at least one line of said first field and said at least one line of said second field, and f) preforming steps a) through e) above for additional lines of said first and second fields.

2. A method in accordance with claim 1, wherein:

said at least one line of said first field comprises two lines both located immediately adjacent to said at least one line of said second field, said value of said at least one pixel in said at least one line of said first field comprises an average of a value of a pixel in one of said two lines and a value of a pixel in another of said two lines, and if said difference exceeds said fixed value, said value of said at least one pixel in said at least one line of said second field is replaced with said average of said values.

3. A processor configured and programmed to process images for display by an interlaced video display device by performing the method of claim 1.

* * * * *